US011565026B2

(12) United States Patent
Yang et al.

(10) Patent No.: US 11,565,026 B2
(45) Date of Patent: Jan. 31, 2023

(54) 3D PRINTING OF BIOMEDICAL IMPLANTS

(71) Applicant: Northwestern University, Evanston, IL (US)

(72) Inventors: Jian Yang, Evanston, IL (US); Evan C. Baker, Chicago, IL (US); Henry O. T. Ware, Shawnee, OK (US); Fan Zhou, Torrance, CA (US); Cheng Sun, Willmette, IL (US); Guillermo A. Ameer, Chicago, IL (US); Robert Van Lith, Evanston, IL (US)

(73) Assignee: Northwestern University, Evanston, IL (US)

( * ) Notice: Subject to any disclaimer, the term of this patent is extended or adjusted under 35 U.S.C. 154(b) by 85 days.

(21) Appl. No.: 17/308,825

(22) Filed: May 5, 2021

(65) Prior Publication Data

US 2021/0346576 A1 Nov. 11, 2021

Related U.S. Application Data

(63) Continuation of application No. 16/795,185, filed on Feb. 19, 2020, now abandoned, which is a (Continued)

(51) Int. Cl.
*A61L 31/06* (2006.01)
*C08J 3/24* (2006.01)
(Continued)

(52) U.S. Cl.
CPC .............. *A61L 31/06* (2013.01); *A61L 31/16* (2013.01); *A61L 31/18* (2013.01); *B29C 41/00* (2013.01); *B29C 41/22* (2013.01); *B29C 64/135* (2017.08); *B29C 64/20* (2017.08); *B33Y 30/00* (2014.12); *B33Y 70/00* (2014.12); *B33Y 80/00* (2014.12);
(Continued)

(58) Field of Classification Search
CPC .......... A61L 31/06; A61L 31/16; A61L 31/18; B29C 41/00; B29C 41/22; B29C 64/135; B29C 64/20; B33Y 30/00; B33Y 70/00; B33Y 80/00; B33Y 10/00; C08J 3/24; C08J 2367/06; C09D 167/06; B29K 2033/00; B29K 2105/0005; B29K 2995/0056;
(Continued)

(56) References Cited

U.S. PATENT DOCUMENTS 8,404,264 B2 3/2013 Ameer
8,568,765 B2 10/2013 Ameer et al.
(Continued)

OTHER PUBLICATIONS

Arshady, Preparation of biodegradable microspheres and microcapsules: 2. Polyactides and related polyesters, Journal of Controlled Release, vol. 17(1), pp. 1-21, 1991.
(Continued)

*Primary Examiner* — Nahida Sultana
(74) *Attorney, Agent, or Firm* — Casimir Jones SC; David W. Staple

(57) ABSTRACT

Provided herein are methods, compositions, devices, and systems for the 3D printing of biomedical implants. In particular, methods and systems are provided for 3D printing of biomedical devices (e.g., endovascular stents) using photo-curable biomaterial inks (e.g., or methacrylated poly (diol citrate)).

2 Claims, 23 Drawing Sheets

Related U.S. Application Data continuation of application No. 15/569,670, filed as application No. PCT/US2016/029774 on Apr. 28, 2016.

(60) Provisional application No. 62/154,499, filed on Apr. 29, 2015.

(51) Int. Cl.
| | |
|---|---|
| *B33Y 80/00* | (2015.01) |
| *B29C 64/135* | (2017.01) |
| *B29C 41/22* | (2006.01) |
| *B29C 41/00* | (2006.01) |
| *B33Y 30/00* | (2015.01) |
| *B33Y 70/00* | (2020.01) |
| *B29C 64/20* | (2017.01) |
| *A61L 31/16* | (2006.01) |
| *A61L 31/18* | (2006.01) |
| *C09D 167/06* | (2006.01) |
| *B29L 31/00* | (2006.01) |
| *B33Y 10/00* | (2015.01) |
| *B29K 33/00* | (2006.01) |
| *B29K 105/00* | (2006.01) |

(52) U.S. Cl.
CPC .............. *C08J 3/24* (2013.01); *C09D 167/06* (2013.01); *B29K 2033/00* (2013.01); *B29K 2105/0005* (2013.01); *B29K 2995/006* (2013.01); *B29K 2995/0056* (2013.01); *B29L 2031/7534* (2013.01); *B33Y 10/00* (2014.12); *C08J 2367/06* (2013.01)

(58) Field of Classification Search
CPC ....... B29K 2995/006; B29L 2031/7534; A61F 2240/001; A61F 2/82
See application file for complete search history.

(56) References Cited

U.S. PATENT DOCUMENTS

| | | | |
|---|---|---|---|
| 8,580,912 B2 | 11/2013 | Ameer et al. | |
| 8,758,796 B2 | 6/2014 | Ameer et al. | |
| 8,772,437 B2 | 7/2014 | Ameer et al. | |
| 8,911,720 B2 | 12/2014 | Ameer et al. | |
| 9,017,312 B2* | 4/2015 | Lee .................... | A61K 31/167 604/891.1 |
| 10,729,823 B2* | 8/2020 | Lee .................... | A61K 9/0004 |
| 11,440,261 B2* | 9/2022 | Wilenski .............. | B29C 64/393 |
| 2006/0022379 A1 | 2/2006 | Wicker et al. | |
| 2006/0188546 A1 | 8/2006 | Giroux | |
| 2008/0255510 A1 | 10/2008 | Wang | |
| 2010/0112068 A1 | 5/2010 | Boyden et al. | |
| 2010/0234529 A1 | 9/2010 | Shelekhov | |
| 2011/0124765 A1 | 5/2011 | Yang et al. | |
| 2011/0212501 A1 | 9/2011 | Yoo | |
| 2012/0089238 A1 | 4/2012 | Kang et al. | |
| 2013/0084449 A1 | 4/2013 | Lewis et al. | |
| 2013/0226277 A1 | 8/2013 | Sun et al. | |
| 2014/0037588 A1 | 2/2014 | Yang et al. | |
| 2014/0093932 A1 | 4/2014 | Murphy et al. | |
| 2014/0135407 A1 | 5/2014 | Ameer et al. | |
| 2014/0155516 A1 | 6/2014 | Ameer et al. | |
| 2016/0046832 A1 | 2/2016 | Wroblesky et al. | |
| 2016/0237245 A1 | 8/2016 | Furo et al. | |
| 2017/0079262 A1 | 3/2017 | Rowley et al. | |
| 2017/0165460 A1* | 6/2017 | Lee .................... | A61M 25/0009 |
| 2017/0247570 A1 | 8/2017 | Pirrung et al. | |
| 2018/0159037 A1 | 6/2018 | McAlpine et al. | |
| 2018/0280578 A1 | 10/2018 | Hwang | |
| 2018/0303616 A1 | 10/2018 | Bhattacharyya et al. | |
| 2019/0008998 A1 | 1/2019 | Cui et al. | |
| 2019/0054536 A1 | 2/2019 | Xu et al. | |
| 2019/0136079 A1 | 5/2019 | Moussa | |
| 2019/0152133 A1 | 5/2019 | Busbee | |

OTHER PUBLICATIONS

Baker et al., Microstereolithography of Three-Dimensional Polymeric Springs for Vibration Energy Harvesting, Smart Materials Research, vol. 2012, article 741835, 2012.

Balashanmugam et al., STL-less based CAD/CAM Approach for Laser Scanning in Micro Stereo Lithography, Procedia Materials Science, vol. 5, pp. 1466-1472, 2014.

Chen et al., Rapidly self-expandable polymeric stents with a shape-memory property, Biomacromolecules. Sep. 2007;8(9):2774-80.

Dendukuri et al., Continuous-flow lithography for high-throughput microparticle synthesis, Nat Mater. May 2006;5(5):365-9.

Garg et al., Coronary Stents: Looking Forward, J Am Coll Cardiol. Aug. 31, 2010;56(10 Suppl):S43-78.

Garg et al., New concepts in the design of drug-eluting coronary stents, Nat Rev Cardiol. May 2013;10(5):248-60.

Grabow et al., A biodegradable slotted tube stent based on poly(L-lactide) and poly(4-hydroxybutyrate) for rapid balloon-expansion, Ann Biomed Eng. Dec. 2007;35(12):2031-8.

Gundogan et al., Bioabsorbable Stent Quo Vadis: A Case for Nano-Theranostics, Theranostics. Feb. 22, 2014;4(5):514-33.

Hermawan et al., Developments in metallic biodegradable stents, Acta Biomater. May 2010;6(5):1693-7.

Holland et al., Polymers for biodegradable medical devices. 1. The potential of polyesters as controlled macromolecular release system, Journal of Controlled Release, vol. 4(3), pp. 155-180, 1986.

Illum et al., "Polymers in Controlled Drug Delivery" Wright, Bristol, 1987.

Kedia et al., Stent thrombosis with drug-eluting stents: a re-examination of the evidence, Catheter Cardiovasc Interv. May 1, 2007;69(6):782-9.

Lim et al., Rapid Prototyping and Tooling of Custom-Made Tracheobronchial Stents, The International Journal of Advanced Manufacturing Technology, vol. 20(1), pp. 44-49, 2002.

Liu et al., Fabrication of balloon-expandable self-lock drug-eluting polycaprolactone stents using micro-injection molding and spray coating techniques, Ann Biomed Eng. Oct. 2010;38(10):3185-94.

Melgoza et al., Rapid tooling using 3D printing system for manufacturing of customized tracheal stent, Rapid Prototyping Journal, vol. 20(1), pp. 2-12, 2014.

Muller et al., Study of inkjet printing as additive manufacturing process for gradient polyurethane materila., Prod. Eng Res. Devel. (2014) 8:25-32.

Ormiston et al., Bioabsorbable coronary stents, Circ Cardiovasc Interv. Jun. 2009;2(3):255-60.

Park et al., In vivo evaluation and characterization of a bioabsorbable drug-coated stent fabricated using a 3D-printing system, Mater Lett, vol. 141, pp. 355-358, 2015.

Pitt, The controlled parenteral delivery of polypeptides and proteins, Int J Pharm, vol. 59(3), pp. 173-196, 1990.

Ranade et al., Physical characterization of controlled release of paclitaxel from the TAXUS™ Express2™ drug-eluting stent, J Biomed Mater Res A. Dec. 15, 2004;71(4):625-34.

Regar et al., Stent development and local drug delivery, Br Med Bull. 2001;59:227-48.

Rengier et al., 3D printing based on imaging data: review of medical applications, Int J Comput Assist Radiol Surg. Jul. 2010;5(4):335-41.

Schmitz et al., Drug-eluting stent technologies for vascular regeneration, Int J Mater Res, vol. 98(7), pp. 637-642, 2007.

Serrano et al., Novel biodegradable shape-memory elastomers with drug-releasing capabilities, Adv Mater. May 17, 2011;23(19):2211-5.

Sigwart et al., Intravascular stents to prevent occlusion and restenosis after transluminal angioplasty, N Engl J Med. Mar. 19, 1987;316(12):701-6.

(56) References Cited

OTHER PUBLICATIONS

Sun et al., Projection micro-stereolithography using digital micro-mirror dynamic mask, Sensors and Actuators A, vol. 121(1), pp. 113-120, 2005.
Surruys et al., Coronary-artery stents, N Engl J Med. Feb. 2, 2006;354(5):483-95.
Umeda., K.I.a.N., Rapid prototyping in Biomedical Engineering, Advanced Applications of Rapid Prototyping Technology in Modern Engineering. 2011.
Venkatraman et al., Biodegradable stents with elastic memory, Biomaterials. Mar. 2006;27(8):1573-8.
Wang et al., Photo-crosslinked Biodegradable Elastomers for Controlled Nitric Oxide Delivery. Biomaterial Science. Jun. 2013;1(6):625-32.
Yang et al., A thermoresponsive biodegradable polymer with intrinsic antioxidant properties, Biomacromolecules. Nov. 10, 2014;15(11):3942-52.
Yang et al., Haemo- and cytocompatibility of bioresorbable homo- and copolymers prepared from 1,3-trimethylene carbonate, lactides, and epsilon-caprolactone, J Biomed Mater Res A. Aug. 2010;94(2):396-407.
Yang et al., Hydrolytic and enzymatic degradation of poly(trimethylene carbonate-co-d,l-lactide) random copolymers with shape memory behavior, Eur Poly J, vol. 46(4), pp. 783-791, 2010.
Yang et al., Synthesis and evaluation of poly(diol citrate) biodegradable elastomers, Biomaterials. Mar. 2006;27(9):1889-98.
Zheng et al., Design and optimization of a light-emitting diode projection micro-stereolithography three-dimensional manufacturing system, Rev Sci Instrum. Dec. 2012;83(12):125001.
International Search Report of related PCT/US2016/29774, dated Jul. 27, 2016, 9 pages.

\* cited by examiner

3D PRINTING OF BIOMEDICAL IMPLANTS

CROSS REFERENCE TO RELATED APPLICATIONS

The present invention is a continuation of U.S. patent application Ser. No. 16/795,185, filed Feb. 19, 2020, which is a continuation of U.S. patent application Ser. No. 15/569,670, filed Oct. 26, 2017, now abandoned, which is a § 371 U.S. National Entry application of PCT/US2016/029774, filed Apr. 28, 2016, which claims priority to U.S. Provisional Patent Application 62/154,373, filed Apr. 29, 2015, each of which is incorporated by reference in its entirety.

FIELD

Provided herein are methods, compositions, devices, and systems for the 3D printing of biomedical implants. In particular, methods and systems are provided for 3D printing of biomedical devices (e.g., endovascular stents) using photo-curable biomaterial inks (e.g., or methacrylated poly (diol citrate)).

BACKGROUND

Biodegradable stents (BDSs"), both metallic and polymeric, offer promising alternatives to conventional bare metal stents (BMSs) and drug-eluting stents (DES s) in providing temporary drug release for vessel patency, resisting late stent thrombosis due to uncovered struts, and potential reduction in the usage of antiplatelet drugs (refs. 4, 9; incorporated by reference in their entireties). Moreover, disappearance of BDS over time allows for eventual recurrence of natural vasomotion.

SUMMARY

Provided herein are methods, compositions, devices, and systems for the 3D printing of biomedical implants. In particular, methods and systems are provided for 3D printing of biomedical devices (e.g., endovascular stents) using photo-curable biomaterial inks (e.g., or methacrylated poly (diol citrate)). In some embodiments, provided herein are systems comprising: (a) a photo-curable biomaterial ink; and (b) a 3D printing device for: (i) dispensing a layer of the photo-curable biomaterial ink in a pattern according to encoded instructions, (ii) exposing the layer of the photo-curable biomaterial ink to light to cure the biomaterial ink and produce a solidified biomaterial layer, and (iii) repeating steps (i) and (ii), with each successive layer built upon the previous layer to produce a 3D structure of the solidified biomaterial. In some embodiments, the photo-curable biomaterial ink comprises methacrylated poly(diol citrate). In some embodiments, the poly(diol citrate) comprises a polymer of citric acid and HO—$(CH_2)_n$—OH, wherein n is 2-20. In some embodiments, the photo-curable biomaterial ink further comprises one or more of: a solvent, a photoinitiator, a co-initiator, a free-radical quencher, and a UV-absorber. In some embodiments, the 3D printing device is configured for laser scanning stereolithography, projection stereolithography, ink-jet printing, continuous liquid interface production, or combinations thereof.

In some embodiments, provided herein is a biomaterial device produced using a system described herein (e.g., biomaterial ink and 3D printing device).

In some embodiments, provided herein are biomaterial inks comprising methacrylated poly (diol citrate), solvent or dilutant, and a photoinitiator. In some embodiments, the poly (diol citrate) is a polymer of citric acid and an aliphatic diol selected from selected from HO—$(CH_2)_n$—OH, wherein n is 2-20. In some embodiments, the methacrylated poly (diol citrate) is present in the biomaterial ink at 50-99 wt % (e.g., 50%, 55%, 60%, 65%, 70%, 75%, 80%, 85%, 90%, 95%, 99%, or ranges therebetween). In some embodiments, the solvent or dilutant is present in the biomaterial ink at 1-49.9 wt % (e.g., 1%, 2%, 3%, 4%, 5%, 10%, 15%, 20%, 25%, 30%, 35%, 40%, 45%, 49%, 49.9%, or ranges therebetween). In some embodiments, the photoinitiator is present in the biomaterial ink at 0.1-5 wt % (e.g., 0.1%, 0.2%, 0.3%, 0.4%, 0.5%, 1%, 2%, 3%, 4%, 5%, or ranges therebetween). In some embodiments, a biomaterial ink further comprises a co-initiator, a free-radical quencher, and/or a UV-absorber. In some embodiments, a biomaterial ink further comprises a radiopacity agent (e.g., iohexyl, iopromide, ioversol, ioxaglate, iodixanol, etc.). In some embodiments, a biomaterial ink further comprises a therapeutic agent (e.g., anticoagulant (e.g., heparin, Coumadin, protamine, hirudin, etc.), antithrombotic agent (e.g., clopidogrel, heparin, hirudin, iloprost, etc.), antiplatelet agent (e.g., aspirin, dipyridamole, etc.), anti-inflammatory agent (e.g., methylprednisolone, dexamethasone, tranilast, etc.), anti-proliferative/immunosuppressive agent (e.g., trapidil, tyrphostin, rapamycin, FK-506, mycophenolic acid), cytostatic drug (e.g., paclitaxel, rapamycin, rapamycin analogs (e.g., everolimus, tacrolimus, etc.), etc.), lipid-lowering agent (e.g., statin), antioxidant (e.g., probucol, vitamin C, retinoids, resveratrol, etc.)).

In some embodiments, provided herein is a biomaterial device produced by the curing of a biomaterial ink described herein.

Definitions

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a mPDC polymer" is a reference to one or more mPDC polymers and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "polymer" refers to a chain of repeating structural units or "monomers", typically of large molecular mass. Examples of polymers include homopolymers (single type of monomer subunits), copolymers (two types of monomer subunits), and heteropolymers (e.g., three or more types of monomer subunits).

As used herein, the term "linear polymer" refers to a polymer in which the molecules form long chains without branches or crosslinked structures.

As used herein, the term "branched polymer" refers to a polymer comprising a polymer backbone with one or more additional monomers, or chains or monomers, extending from polymer backbone. The degree of interconnectedness of the "branches" is insufficient to render the polymer insoluble.

As used herein, the term "pre-polymer" refers to linear or branched polymers (e.g., not significantly crosslinked) that have the capacity to be crosslinked under appropriate conditions (e.g., to form a thermoset), but have not been subjected to the appropriate conditions.

As used herein, the term "crosslinked polymer" refers to a polymer with a significant degree of interconnectedness between multiple polymer strands, the result of which is an insoluble polymer network (e.g., a thermoset). For example, multiple polymer stands may be crosslinked to each other at points within their structures, not limited to the ends of the polymer chains. In some embodiments, two or more different polymers may be crosslinked.

As used herein, the terms "composite" and "composite material" refer to materials or compositions generated from the combination of two or more constituent materials (e.g., compounds, polymers, etc.). The constituent materials may interact (e.g., non-covalently) at the microscopic or molecular level, but typically do not react chemically (e.g., covalently). At the macroscopic level, the constituent materials appear homogenous.

As used herein, the term "biocompatible" refers to materials, compounds, or compositions means that do not cause or elicit significant adverse effects when administered to a subject. Examples of possible adverse effects include, but are not limited to, excessive inflammation, excessive or adverse immune response, and toxicity.

As used herein, the term "biostable" refers to compositions or materials that do not readily break-down or degrade in a physiological or similar aqueous environment. Conversely, the term "biodegradable" refers herein to compositions or materials that readily decompose (e.g., depolymerize, hydrolyze, are enzymatically degraded, disassociate, etc.) in a physiological or other environment.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

DETAILED DESCRIPTION

Figure 1:
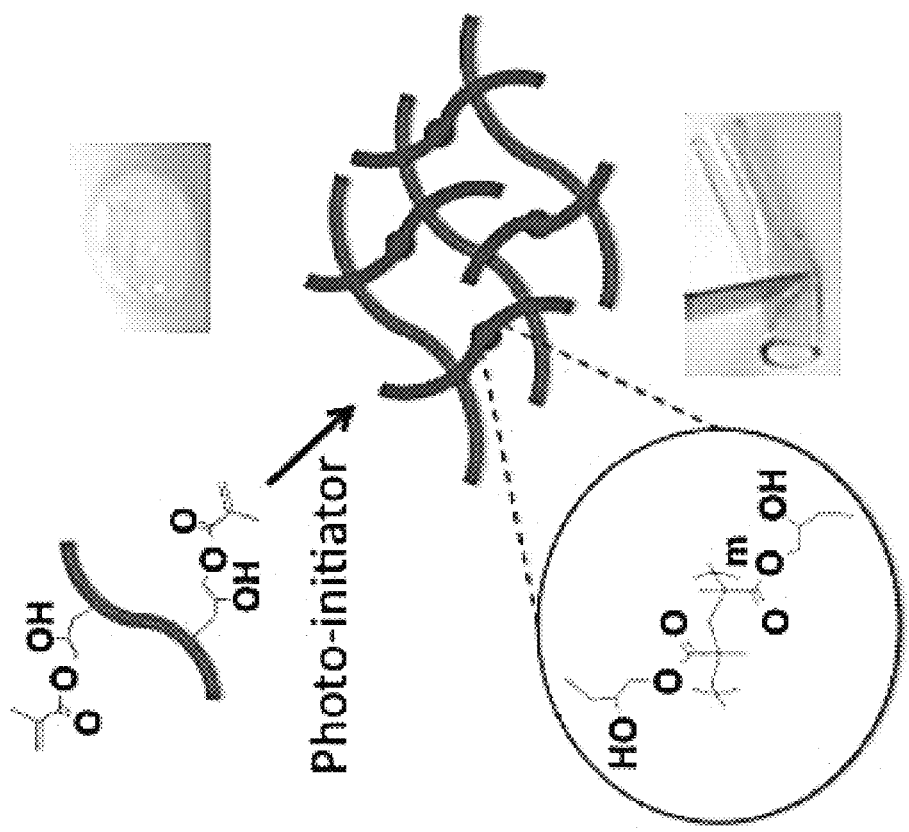
FIG. 1. Chemical structure and proton nuclear magnetic resonance spectrum of methacrylated poly(1,12-dodecanediol citrate) polymer (left); schematic showing the reaction due to exposure to UV (right).
Figure 1:
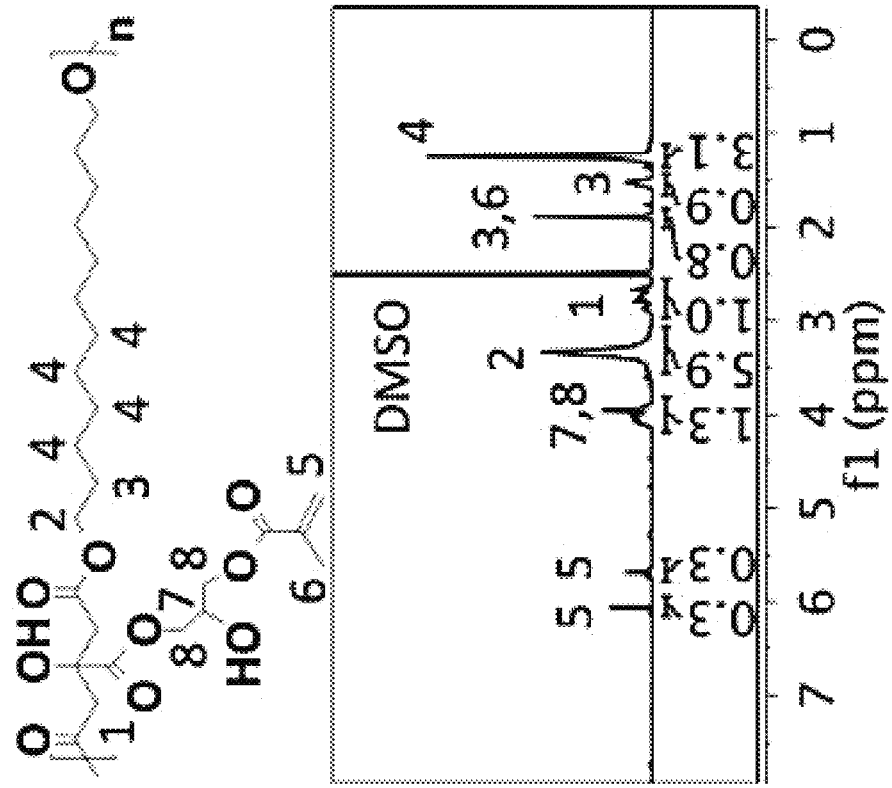

Provided herein are methods, compositions, devices, and systems for the 3D printing of biomedical implants. In particular, methods and systems are provided for 3D printing of biomedical devices (e.g., endovascular stents) using photo-curable biomaterial inks (e.g., or methacrylated poly (diol citrate)).

Among natural and synthetic biodegradable polymers, chitosan, poly(4-hydroxybutyrate) (PHB), poly(ε-caprolactone) (PCL), poly(L-lactide) (PLLA) and poly(D,L-lactide) (PDLLA) and its copolymers or composites have been extensively investigated for use in resorbable devices (refs. 10-16; incorporated by reference in their entireties). In particular, a polylactide stents (e.g., Igaki Tamai or bioabsorbable vascular stents (BVSs)) have been shown to degrade into metabolites such as lactic acid, $CO_2$ and $H_2O$ in two years and testing indicates they are safe when used in human coronary arteries (ref.13; incorporated by reference in its entirety). Relative to a BMS, the self-expandable PLLA stents require 8 min for full-expansion in an aqueous environment due to the viscoelastic behavior of polymer 37° C. (ref. 17; incorporated by reference in its entirety), which increases the risk of ischemia and myocardial infarction. Late shrinkage after degradation also remains a concern. As with metal stents, there are manufacturing challenges for strut design, processing, and fabrication.

Rapid prototyping techniques such as stereolithography, selective laser sintering, fused deposition modeling and others have been developed for high precision manufacturing of customized biomedical devices, greatly expanding in biomedical research and tissue engineering for a broad range of functional and structural materials such as hydrogels, polymers and ceramics (refs. 18, 19; incorporated by reference in their entireties). Continuous tool path planning strategies have been optimized for open sourced and commercial fused deposition machines (FDM), making a customized tracheal stent rapidly and affordably (ref. 20; incorporated by reference in its entirety). In comparison to selective laser sintering and solid ground curing, stereolithography offered the best surface finish in the process of customized tracheobronchial stents, while selective ground curing had the best repeatability of length (ref. 21; incorporated by reference in its entirety). Unlike the above large-size stents, a bioabsorbable drug-coated stent was manufactured with a 300 um strut diameter using PCL polymer and a rapid prototyping technique (ref. 22; incorporated by reference in its entirety). These stents showed to be effective in reducing neointimal hyperplasia, inflammation and thrombosis formation. A 3D micro-jetting free molding technique has been developed to fabricate slide or snap fastener biodegradable stents with polydioxanone (PDO) (ref. 23; incorporated by reference in its entirety). Different from extrusion techniques in 3D printing, projection microstereolithography (PµSL) offers a high precision and high resolution processing method with a digital micromirror device (DMD™, Texas Instruments) as a dynamic mask (refs. 24, 25; incorporated by reference in their entireties)].

Provided herein are methods for rapid fabrication of biomedical devices (e.g., implants (e.g., endovascular stents), etc.) using biomaterial ink and 3D printing or additive manufacturing processes with micrometer accuracy. Provided herein are biomaterial inks that are suitable for 3D printing processes, digital representation of stent design using Computer-aid design (CAD) modeling, devices (e.g., stents) with optimized mechanical properties using, for example, numerical simulation, fabrication processing parameters for device prototype and scalable manufacturing biomaterial ink that is photopolymerized by ultraviolet or visible light at various wavelengths, etc. Different structures (e.g., stent structures), such as sinusoidal formed wire, helical wrap, and/or laser-fused struts are obtainable and customizable with patient-specific features in the CAD model and subsequently fabricated using 3D printing systems with high fidelity. By optimizing the stent geometry, biomaterial ink compositions (e.g., polydiolcitrate solution composition), initiator concentration, and curing conditions, the mechanical properties of printed devices (e.g., stents) are tailored to closely match with blood vessel or a bare metal stent. In some embodiments, kink-resist stents are obtained by incorporating the stent strut exhibiting near-zero or negative Poisson's ratio. In some embodiments, the use of biodegradable materials allows for the encapsulation and slow release of drugs or other agents from the bulk of the stent rather than a coating that is applied to the stent struts.

In some embodiments, using photo-curable polymers, complex 3D microstructures are created. A series of citrate-based polymers with a wide range of properties such as controllable elasticity, biodegradability, shape-memory and antioxidant properties have been developed [26, 27; incorporated by reference in their entireties], and find use in embodiments herein. After methacrylation with glycidyl methacrylate, 2-aminoethyl methacrylate, or another suitable compound, polymers are printed (e.g., via projection stereolithography, via Micro-CLIP, etc.) under the appropriate solvent and additive conditions. Exemplified herein are compositions and methods to feasibly 3D print complex strut structures of biodegradable polymers on a micron scale.

Embodiments herein find use in, for example: endovascular stents and stent-related implants, 3D printed biomedical implants containing patient-specific features, tailoring the mechanical properties of 3D printed devices through structural and materials design, related 3D printed products derived from biocompatible and/or biodegradable biomaterial inks, 3D printed bio-medical implants for sustained drug release, in vivo sensing platforms, etc.

Advantages of some embodiments herein include: the building materials of the 3D printed stent are precisely tailored to exhibit a compliant compressive, strength and flexibility with blood vessel and bare metal stent, the use of biodegradable biomaterial ink allows for the encapsulation of therapeutic agents, allowing, for example, the slow release of drugs from the bulk of the device (e.g., stent) in contrast, to the state-of-the-art coating method to coat the drug on the surface of stent struts.

Embodiments herein utilize various 3D printing and/or additive manufacturing to create biocompatible and biodegradable devices from compositions comprising biomaterial inks for use, for example, in various biomedical applications. In some embodiments, a biomaterial ink comprises a curable (e.g., chemically-curable, photo-curable, etc.) polymer material. In some embodiments, the biomaterial ink comprises a polymer component displaying one or more curable (e.g., chemically-curable, photo-curable, etc.) substituents; upon exposure of the biomaterial ink to curing conditions, the biomaterial ink is converted from a pre-polymer into an insoluble, crosslinked polymeric material.

In some embodiments, compositions and composites (e.g., biomaterial ink and/or solid biomaterials produced therefrom) described herein comprise a polymeric component. In some embodiments, a polymeric component comprises a polymer selected from a polyester, poly(diol citrate) (e.g., poly(butanediol citrate), poly(hexanediol citrate), poly (octanediol citrate), poly(decanediol citrate), poly(dodecanediol citrate), poly(hexadecanediol citrate), etc.), poly (hydroxyvalerate), poly(lactide-co-glycolide), poly (hydroxybutyrate), poly(hydroxybutyrate-co-valerate), polyorthoester, polyanhydride, poly(glycolic acid), poly (glycolide), poly(L-lactic acid), poly(L-lactide), poly(D,L-lactic acid), poly(D,L-lactide), poly(caprolactone), poly(trimethylene carbonate), polyester amide, or co-polymers or composites thereof.

In some embodiments, a polymeric component comprises a citric acid-based polymer. In some embodiments, a polymer is the polyesterification product of one or more acids (e.g., succinic acid, glutaric acid, adipic acid, pimelic acid, suberic acid, azelaic acid, sebacic acid, dodecanedioic acid, shorter or longer linear aliphatic diacids, citric acid, isocitric acid, aconitic acid, propane-1,2,3-tricarboxylic acid, trimesic acid, itaconic acid, maleic acid, etc.) and one or more diols or triols (e.g., polyethylene glycol, glycerol, linear aliphatic diol (e.g., butanediol, hexanediol, octanediol, decanediol, dodecanediol, and shorter or longer linear aliphatic diols), etc.).

In some embodiments, a polymer is the polyesterification product of at least citric acid and one or more linear aliphatic diols (butanediol, hexanediol, octanediol, decanediol, dodecanediol, or any linear aliphatic diol from about 2-20 carbons in length). A polymer may comprise only citric acid and linear aliphatic diol components or may further comprise additional monomer components (e.g., sebacic acid, polyethylene glycol, glycerol, etc.). In some embodiments, a polymer comprises additional substituents or functional groups appended to the polymer (e.g., ascorbic acid, glycerol, a NONOate group, etc.).

In some embodiments, a polymeric component comprises citric acid as a monomer (e.g., along with a diol monomer). Citric acid is a reactive tricarboxylic acid that is part of the Krebs cycle and has been used as a key reactant monomer for the synthesis of polydiolcitrates with a wide range of properties and uses (Yang, J., et al., Synthesis and evaluation of poly(diol citrate) biodegradable elastomers. Biomaterials, 2006. 27(9): p. 1889-98; U.S. Pat. Nos. 8,772,437; 8,758, 796; 8,580,912; 8,568,765; U.S. Pub. No. 2014/0155516; U.S. Pub. No. 2014/0135407; herein incorporated by reference in their entireties). Depending on the diol of choice, materials with controllable elasticity, biodegradability, and antioxidant properties can be developed (Serrano et al. Adv Mater, 2011. 23(19): p. 2211-5; Yang J., et al., A thermoresponsive biodegradable polymer with intrinsic antioxidant properties. Biomacromolecules, 2014. 15(11):3942-52; U.S. Pub. No. 2014/0037588; herein incorporated by reference in its entirety).

In some embodiments, a polymeric component is a poly (diol citrate), for example, those described in U.S. Pat. No. 8,911,720; herein incorporated by reference in its entirety. In some embodiments, derivatives of such poly(diol citrates) are provided. In some embodiments, a pre-polymer of citric acid and diol is formed (e.g., by reaction at about 140° C. or other suitable conditions). In some embodiments, a pre-polymer is reacted with one or more additional compounds to produce a functionalized (e.g., methacrylated) pre-polymer.

As addressed above, in some embodiments, the curable polymer component of a biomaterial ink comprises a polymer displaying one or more curable (e.g., chemically-curable, photo-curable, etc.) groups. In some embodiments, a curable group is or comprises a methacrylate or acrylate group. In some embodiments, a curable group is or comprises Vinylpyrrolidone (NVP) or styrenestyrene.

In some embodiments, a pre-polymer (e.g., of poly(diol citrate)) is reacted (e.g., at about 40-100° C.) with a modifying group to produce a poly(diol citrate) polymer displaying a curable substituent group (e.g., methacrylate) and/or crosslinked to form an elastomer displaying the substituent group. In some embodiments, suitable reactant for modifying the poly(diol citrate) pre-polymer is glycidyl methacrylate or 2-aminoethyl methacrylate. In some embodiments, poly(diol citrate) and glycidyl methacrylate (or 2-aminoethyl methacrylate) are reacted in the presence of tetrahydrofuran and imidazole. Other substituents (e.g., other than glycidyl methacrylate) may also be reacted with the poly (diol citrate) (e.g., alone or with glycidyl methacrylate), and/or other polymer components may be methacrylated. In some embodiments, rather than methacrylation, and acrylate group is displayed on the polymer or pre-polymer to produce a curable polymer for a biomaterial ink.

In some embodiments, a citric acid-based, curable polyester comprises:

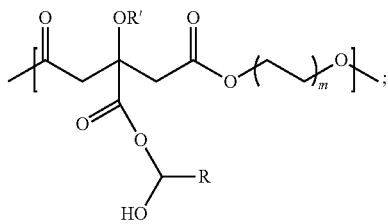

wherein R is selected from H, a poly(diol citrate), and a curable group (e.g., photo-curable group (e.g., methacrylate group)); wherein R' is selected from H, and a poly(diol citrate); wherein m is 2 to 20; and wherein at least one R is a curable group (e.g., photo-curable group (e.g., methacrylate group)).

In some embodiments, the citric acid-based polyester comprises:

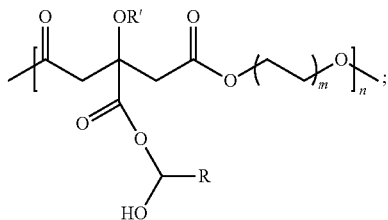

wherein R is selected from H, a poly(diol citrate), and a curable group (e.g., photo-curable group (e.g., methacrylate group)); wherein R' is selected from H, and a poly(diol citrate); wherein m is 2 to 20; wherein n is 1 to 1000, and wherein 1-100% (e.g., 1%, 2%, 5%, 10%, 15%, 20%, 30%, 40%, 50%, 60%, 70%, 80%, 90%, 95%, 99%, 100%) of R groups are a curable group (e.g., photo-curable group (e.g., methacrylate)). In some embodiments, at least one R group comprises a methacrylate. In some embodiments, the citric acid-based polyester comprises:

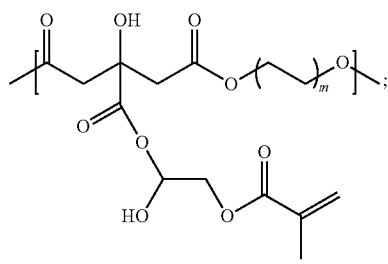

wherein m is 2 to 20.

In some embodiments, the citric acid-based polyester comprises:
the citric acid-based polyester comprises:

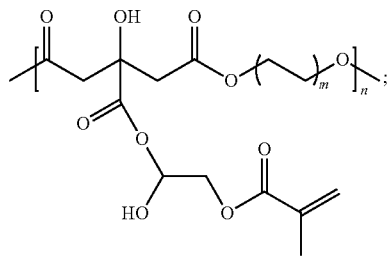

wherein m is 2 to 20; and wherein n is 1 to 1000. In some embodiments, m is 6 to 14.

In some embodiments, provided herein are methods of preparing methacrylated poly(diol citrate) comprising: a) synthesizing a prepolymer of citric acid and an aliphatic diol; and b) reacting the prepolymer with glycidyl methacrylate or 2-aminoethyl methacrylate. In some embodiments, the aliphatic diol is $HO(CH_2)_zOH$, wherein z is 2-20.

In some embodiments, in addition to a curable (e.g., photocurable) polymer component, a biomaterial ink comprises one or more of: a suitable solvent, a photoinitiator, a co-initiator, a free-radical quencher, a UV-absorber, etc. In some embodiments, suitable additional components of a biomaterial ink include ethyl acetate, 1-butanol, Diethyl adipate, 1,6-hexanediol diacrylate, Diethyl fumarate, Irgacure 819, 2-hydroxy-2-methylpropiophone (Homp), Camphorquinone, 4-ethyl-N,N-dimethylaminobenzoate, dyes such as Yellow 5 and Sudan 1, etc. Additional components will be understood in the field.

In some embodiments, a biomaterial ink comprises one or more non-curable polymers or other materials, in addition to the photo-curable polymer component. In some embodiments, upon curing of the biomaterial ink, a composite (e.g., noncovalently association) is formed between the cured polymer component and the non-curable component. In some embodiments, the non-curable component is stabilized within the composite by the cured polymer. Therefore, in some embodiments, biomaterial inks and the cured composites thereof may comprise curable (or cured) polymer component and one or more additional compounds, oligomers, polymers, hydrogels, thermosets etc. For example, biomaterial inks (and materials formed therefrom) may comprise one or more biodegradable polymers to form a composite material. Suitable biodegradable polymers include, but are not limited to: collagen, elastin, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), poly(diol citrate) (e.g., poly(octanediol citrate), etc.), casein, dextran and derivatives, polysaccharides, poly(caprolactone), fibrinogen, poly(hydroxyl acids), poly(L-lactide) poly(D,L lactide), poly(D,L-lactide-co-glycolide), poly(L-lactide-co-glycolide), copolymers of lactic acid and glycolic acid, copolymers of ε-caprolactone and lactide, copolymers of glycolide and ε-caprolactone, copolymers of lactide and 1,4-dioxane-2-one, polymers and copolymers that include one or more of the residue units of the monomers D-lactide, L-lactide, D,L-lactide, glycolide, ε-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly (malic acid), poly(tartronic acid), polyanhydrides, polyphosphazenes, poly(amino acids), and copolymers of the above polymers as well as blends and combinations of the above polymers (See generally, Ilium, L., Davids, S. S. (eds.) "Polymers in Controlled Drug Delivery" Wright, Bristol, 1987; Arshady, J. Controlled Release 17:1-22, 1991; Pitt, Int. J. Phar. 59:173-196, 1990; Holland et al., J. Controlled Release 4:155-0180, 1986; herein incorporated by reference in their entireties). Composites of the curable (or cured) polymer and non-polymeric materials are also within the scope of embodiments described herein. Such non-polymer components include, but are not limited to a bioceramic (e.g., hydroxyapatite, tricalcium phosphate, etc.), nanoparticles (e.g., iron oxide, zinc oxide, gold, etc.), etc.

In some embodiments, the curable (or cured) polymer comprises at least 10% (e.g., 10%, 20%, 30%, 40%, 50%, 60%, 70%, 80%, 90%, 95%, 98%, 99%, 100%) of the biomaterial ink and/or the resulting cured biomaterial. The aforementioned percentages may be wt % or molar %.

In some embodiments, many characteristics of the devices made with the materials and methods described herein are customizable. For example, to enable visibility of stents in the operating room, the radiopacity if the materials was considered. To enable radiopacity of stents (or other devices and implants), a large variety of possible materials could be used. In experiments conducted during development of embodiments herein, visipaque and Iodixanol have been incorporated devices (e.g., stents). One issue with stents that are used currently is that a stent exhibiting radiopacity blocks the view of a variety of scanning techniques that doctors use to determine the extent of restenosis. Since the device and stents herein will absorb into the body, restenosis rates are more easily monitored to determine if and when an additional follow-up procedure is necessary to protect the patient's health.

In additional to radiopacity, in some embodiments, devices comprise materials to serve as contrast agents. This allows the devices to be monitored by various biophysical techniques, such as x-ray, magnetic resonance imaging (MRI), positron emission tomography (PET), computed tomography (CT), or single-photon emission computed tomography (SPECT). Any suitable contrast agent could be incorporated into the materials and devices described herein. For example, in some embodiments, an iodinated contrast agent is incorporated into the materials and devices, such as one selected from the group consisting of iohexyl, iopromide, ioversol, ioxaglate and iodixanol.

Other agents may be incorporated into the biomaterial inks, materials and devices herein. These agents may be covalently attached to a component of the ink (e.g., the polymer component), embedded within the material, coated onto a device, etc. Suitable agents include, but are not limited to: anticoagulants (e.g., heparin, Coumadin, protamine, hirudin, etc.), antithrombotic agents (e.g., clopidogrel, heparin, hirudin, iloprost, etc.), antiplatelet agents (e.g., aspirin, dipyridamole, etc.), anti-inflammatory agents (e.g., methylprednisolone, dexamethasone, tranilast, etc.), anti-proliferative/immunosuppressive agents (e.g., trapidil, tyrphostin, rapamycin, FK-506, mycophenolic acid), cytostatic drugs (e.g., paclitaxel, rapamycin, rapamycin analogs (e.g., everolimus, tacrolimus, etc.), etc.), lipid-lowering agents (e.g., statins), antioxidants (e.g., probucol, vitamin C, retinoids, resveratrol, etc.) etc.

Figure 22:
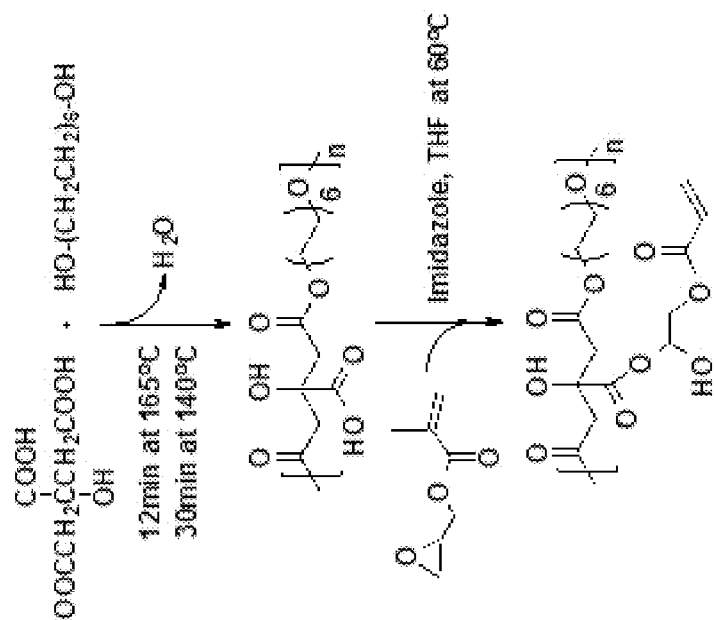
FIG. 22. Exemplary synthesis of methacrylated poly(diol citrate).

In some embodiments, an mPDC base polymer, and any polydiolcitrates or methacrylated poly(diol citrates), are intrinsically antioxidant, which was confirmed by incubating mPDC (50 mg/mL) in 2,2'-azino-bis(3-ethylbenzothiazoline-6-sulphonic acid) or ABTS radical solution. mPDC slowly neutralized free radicals over time with 70% scavenged after 14 days (FIG. 22—Left). To assess the biocompatibility, UV-cured mPDC films were sterilized and seeded with vascular smooth muscle cells. Cells could attach and spread and showed excellent viability after 3 days of cell culture (FIG. 22—Center). 3D-printed stents (composition: 50% DEF, 47.78% mPDC, 2.2% Irgacure 819, 0.02% Sudan I) degraded over time upon incubation in PBS at 37° C., with approximately 25% degraded after 6 months (FIG. 22—Right). These unique characteristics of mPDC makes it a particularly interest candidate for fabricating the bioresorbable scaffolds.

In some embodiments, systems, devices, and methods are provided for fabricating biomaterial devices (e.g., implants, stents, etc.) of defined shapes and dimensions from a curable (e.g., photo-curable) biomaterial ink. Although projection micro-stereolithography (PμLS) and micro-continuous liquid interface production (micro-CLIP) are exemplified in Example 1 and Example 2 below, the scope of embodiments herein are not limited to such systems and methods. Any suitable systems, devices, and methods for the controlled application and of biomaterial ink and conversion of the biomaterial ink into a biomaterial device is within the scope of embodiments herein. Exemplary systems and processes, all or a portion of which may be utilized in embodiments herein, are described in connection with the biomaterial inks and device-production embodiments herein.

In some embodiments, systems, methods, and devices from laser scanning stereolithography techniques are utilized. In such systems, curing between polymers is induced by micro-stereolithography, under the action of light. In some embodiments, a laser scanning unit exposes a defined area on the surface of the biomaterial ink, in a desired pattern, and in that way, with a given depth of penetration, hardens a layer of the pattern to be produced into a solid biomaterial. A displacement unit in the z-direction provides that the substrate is lowered layer by layer by the defined layer thickness or the laser focus is raised. In a processing step, the biomaterial ink, over the previously produced solid biomaterial layer. This process is repeated until the desired structure is produced. Laser scanning stereolithography techniques which may be employed, alone or in combination with other 3D printing and/or additive manufacturing systems and processes are further described in Balashanmugan et al. Procedia Materials Science, Volume 5, 2014, Pages 1466-1472; which is incorporated by reference in its entirety.

In some embodiments, systems, methods, and devices from projection micro-stereolithography techniques are utilized (See, e.g., Example 1). Projection micro-stereolithography (PµSL) adapts 3D printing technology for microfabrication. Digital micro display technology provides dynamic stereolithography masks that work as a virtual photomask. This technique allows for rapid photopolymerization of an entire layer with a flash of UV illumination at micro-scale resolution. The mask controls individual pixel light intensity, allowing control of material properties of the fabricated structure with desired spatial distribution. The dynamic mask defines the beam. In some embodiments, the beam is focused on the surface of a UV-curable polymer resin through a projection lens that reduces the image to the desired size. In some embodiments, once a layer is polymerized, the stage drops the substrate by a predefined layer thickness, and the dynamic mask displays the image for the next layer on top of the preceding one. This proceeds iteratively until complete. PµLS techniques which may be employed, alone or in combination with other 3D printing and/or additive manufacturing systems and processes are further described in Zheng et al. Rev Sci Instrum. 2012 December; 83(12):125001; which is incorporated by reference in its entirety.

In some embodiments, systems, methods, and devices from direct inkjet 3D printing techniques are utilized. Direct inkjet printing systems fabricating a part/device by an additive manufacturing process. For example, in some embodiments, an ink delivery system operative to circulate the biomaterial ink, a printhead associated with the ink delivery system, dispenses the biomaterial through one or more nozzles based on a defined pattern (e.g., CAD defined pattern) onto a surface for receiving the dispensed biomaterial ink one layer at a time. In the case of the curable (e.g., photo-curable) biomaterial inks herein, the dispensed ink is exposed to a cure-induced (e.g., light) in order to produce a layer of solid biomaterial on the receiving surface. The part/device is formed from a plurality of layers, as the biomaterial ink is dispensed from the printhead and the ink is cured in successive layers. PµLS techniques which may be employed, alone or in combination with other 3D printing and/or additive manufacturing systems and processes are further described in Müller et al. Prod. Eng Res. Devel. (2014) 8:25-32; which is incorporated by reference in its entirety.

In some embodiments, systems, methods, and devices from Continuous Liquid Interface Production (CLIP) and/or Micro Continuous Liquid Interface Production (Micro-CLIP) techniques are utilized. In CLIP, the continuous process begins with a pool of photo-curable biomaterial ink. A portion of the pool bottom is transparent ("window") to light (e.g., UV light). A light beam shines through the window, illuminating a precise cross-section of the object. The light converts the biomaterial ink into a sold biomaterial. The formed object rises slowly enough to allow the ink flow under and maintain contact with the bottom of the object. In some embodiments, an oxygen-permeable membrane lies below the ink, creating a "dead zone" (persistent liquid interface) preventing the ink from attaching to the window. PµLS techniques which may be employed, alone or in combination with other 3D printing and/or additive manufacturing systems and processes are further described in Dendukuri, D. (2006). *Nature Materials* 5, 365-369 (2006); which is incorporated by reference in its entirety.

The devices, elements, systems, methods, techniques, etc. from any of the aforementioned 3D printing techniques may be utilized in any combination in embodiments herein.

Due to the biodegradable and biocompatible nature of the materials described herein, the devices and components produced by the systems, materials, and methods herein find particular utility in biomedical applications. In some embodiments, devices or components/parts of devices for implantation into a subject are produced by the systems and methods described herein. Depending upon the particular biomaterial selected, the permanence/impermanence of the particular device may be tailored (e.g., biodegradation over 1 week, 2 weeks, 1 month, 2 months, 3 months, 4 months, 6 months, 8 months, 1 year, 2 years, 3 years, 5 years, 10 years, or ranges therebetween). Embodiments herein are not limited by the type of device or implant, or component/part thereof, that is produced by the systems, materials, and methods described herein. Exemplary implants, devices, etc. that may be manufactured by the systems, materials, and methods described herein, or may have a part or components that may be manufactured by the systems, materials, and methods described herein, include, but are not limited to: stents, stent-grafts, grafts, vascular grafts, shunts, screws, nails, threads, clasps, tubes, catheters, patches, plates, sheets, meshes, ports, rings, prostheses, contact lenses, ocular implants, cardiovascular implants, pacemakers, orthopedic implants, sockets and counterparts, etc.

Although the systems, materials, and methods described herein have particular utility in biomedical applications, embodiments within the scope herein are not so limited. In some embodiments, devices and parts produced by the systems, materials, and methods herein find use in the fields of veterinary medicine, laboratory research, microfluidics, environmental science, industrial, and other applications.

Figure 20:
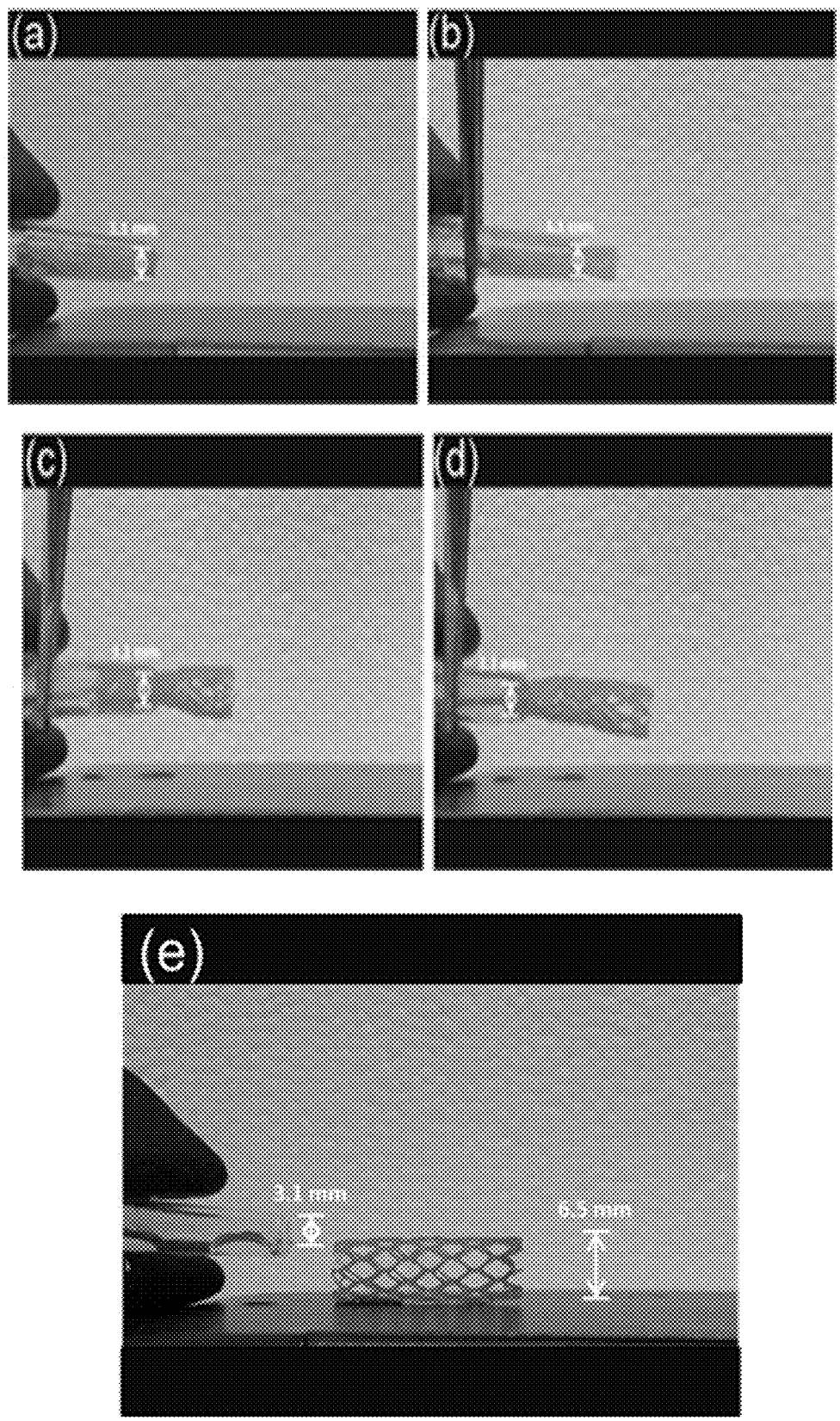
FIG. 20(a-e). Temporal series of images showing sheathing through compression of a 6.5 mm outer diameter stent to 3.1 mm, and subsequent self-expansion upon sheath retraction of 3D-printed stent. Full expansion to original diameter reached in approximately 3 minutes.
Figure 21:
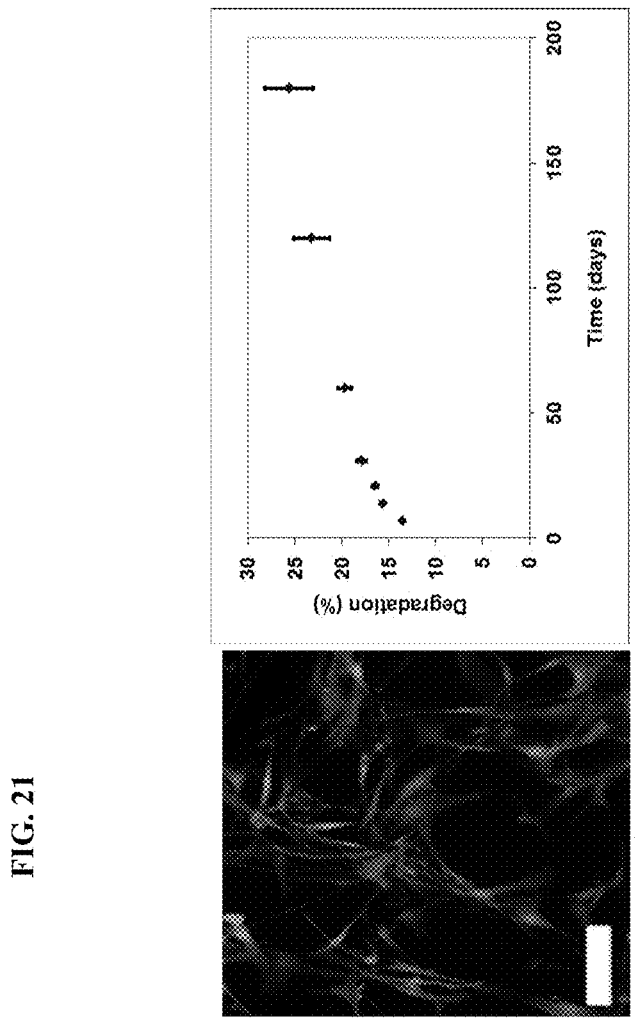
FIG. 21. The 3D-printed stents from mPDC are antioxidant, biocompatible and biodegradable: Left) mPDC scavenges 2,2'-azino-bis(3-ethylbenzothiazoline-6-sulphonic acid) (ABTS) free radical, Center) Human smooth muscle cells on mPDC show good spreading and viability. Scale=100 um, and Right) 3D-printed stents degrade in PBS at 37° C., with approximately 25% degraded after 6 months incubation.

In some embodiments, materials and devices are provided with self-expanding material properties, shown in FIG. 20. In some embodiments, the devices (e.g., stents) are designed and printed in the fully expanded state and then sheathed or compressed into a collapsed conformation (e.g., within a catheter). In some embodiments, the self-expanding character is useful for implantable devices (e.g., stents), for example, for derives that are implanted into peripheral arteries, especially when those arteries are near areas of the body that can be collapsed by external forces such as the arteries within the thigh and near the knees.

In some embodiments, devices are provided comprising balloon-expandable designs. In some embodiments, balloon-expandable devices comprise a PLLA-based material that is plastically deformable. Balloon-expandable stents, for example, are used almost exclusively in cardio implants, and are preferred in that field due to their improved flexibility and stronger radial strength.

EXPERIMENTAL

While the compositions and methods described herein may find use with any suitable photo-polymer based additive manufacturing devices/techniques (e.g., Laser Scanning Stereolithography, Projection Stereolithography, Ink-Jet Printing, Continuous Liquid Interface Production (CLIP), etc.), two printer types are exemplified below to demonstrate successful fabrication, imaging and mechanical testing of the designs to validate them. Exemplary methodologies and utilities of each printing type are explained in the examples below.

The following examples provide exemplary embodiments within the scope herein, and data representing experiments conducted during development of such embodiments. These data exemplify the embodiments herein, but should not be viewed as limiting on the scope of embodiments herein.

Example 1

Projection Micro-Stereolithography

A biodegradable biomaterial ink was formulated with biodegradable methacrylated poly(diol citrate)s and enables rapid fabrication of endovascular devices (e.g., stents) via projection microstereolithography technique. As exemplary devices, stents with various microstructures were printed in a resolution of 20 um using CAD modeling. mPDC stent showed a compliant compressive strength and flexibility. Compared with bare metal stent, numerical simulation showed the experimental results differed by approximately a factor of 5, the 350 um stent best approximates the Nitinol BMS stent.

Polymer Synthesis and Characterization

The synthesis of methacrylated poly(1,12-dodecanediol citrate) is depicted in FIG. 22. A similar scheme is applicable to the methacrylation of other poly(diol citrates), which find use in other embodiments herein.

Citric acid (76.8 g; Sigma) and 1,12-dodecanediol (40.4 g; Sigma) were added to a flask and heated to 165° C. under nitrogen atmosphere. After melting, the reaction was continued for an additional 30 minutes at 140° C. The viscous poly(1,12-dodecanediol citrate) (PDC) pre-polymer is dissolved in 100-150 ml ethanol and purified by precipitation in 1000 mL of deionized water (Millipore water purification system), then freeze-dried for at least 72 hours. Subsequently, 22 g PDC was added to 180 mL tetrahydrofuran (Sigma) for dissolution, then 816 mg of imidazole (Sigma) and 17.04 g of glycidyl methacrylate (Sigma) was added and heated to 60° C. for 6 hours then placed on a rotary evaporator for 30 minutes at 60° C. After methacrylation, mPDC was purified using 900 mL of deionized water twice, then centrifuged in 50 mL vials for 5 minutes at 3500 rpm followed by freeze drying for 24 hours. The purified mPDC polymer was characterized using a Bruker Ag500 NMR spectrometer at ambient temperature, using DMSO-d6 as solvent, and tetramethylsilane (TMS) as the internal reference.

Biomaterial Ink Formulation and Rheological Characterization

The viscous mPDC polymer was diluted with different chemicals such as ethyl acetate (Anhydrous, 99.8%; Sigma), 1-butanol (ACS reagent, >99.4%; Sigma), Diethyl adipate (ReagentPlus®, 99%; Aldrich), 1,6-hexanediol diacrylate (Technical grade, 80%; Aldrich) and Diethyl fumarate (98%; Aldrich), 0.1-5 wt % amounts of initiators such as Irgacure 819, 2-hydroxy-2-methylpropiophone (Homp) and Camphorquinone were formulated into mPDC solution for curing at different wavelengths. Compatibly, 4-ethyl-N,N-dimethylaminobenzoate was used as a co-initiator to accelerate the reaction, a number of dyes such as Yellow 5 and Sudan 1 served as a free radical quencher or UV absorber. The UV/Vis absorption spectra of different initiators were recorded in an Aligent Cary 100 spectrophotometer. Rheological measurement of mPDC solution in ethyl acetate was carried out on a TA instruments DHR rheometer with a 20 mm 4° cone peltier plate geometry and solvent trap cover to minimize sample evaporation. A flow ramp experiment was performed for 0.1 to 142.665 rad/s at 25° C. and 37° C. to determine the dynamic viscosities of pure mPDC and mPDC solution with 5 wt %, 10 wt % and 15 wt % ethyl acetate. Viscosity changes as a function of shear rate were assessed via rheometry.

Projection Microstereolithography Printer Design and Fabrication

Projection microstereolithography (PµSL) builds microstructures from a photo-curable biomaterial ink in a layer-by-layer fashion directly from a 3D CAD design. Each layer is cured in a single exposure by using a liquid crystal display (LCD) panel as a dynamic mask for the UV light. This allows for a drastic reduction in fabrication time compared with conventional 3D printing process, which fabricates 3D structures in a point-by-point scanning fashion.

Figure 7:
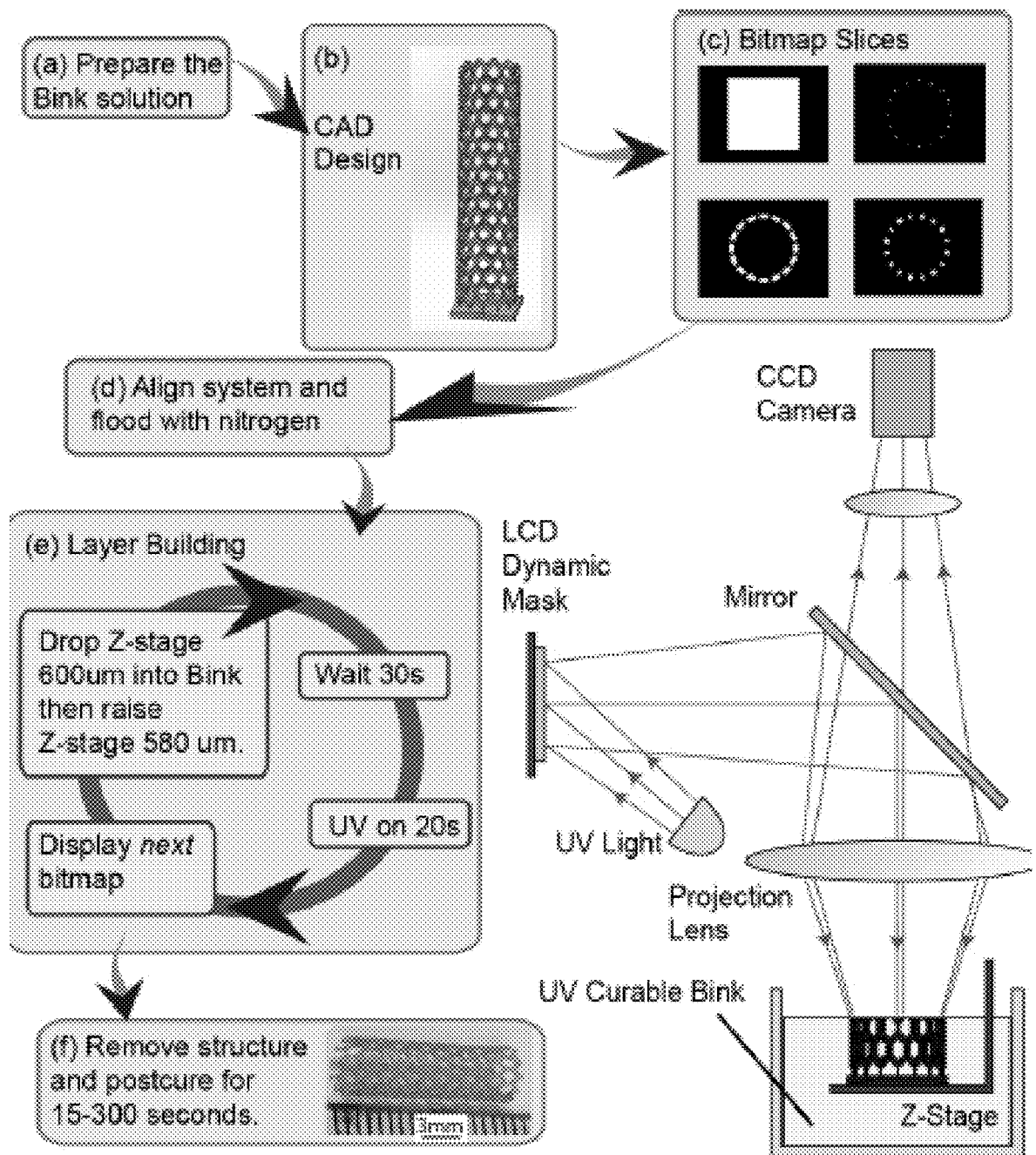
FIG. 7. Exemplary process for stent generation by the methods described herein.
Figure 8:
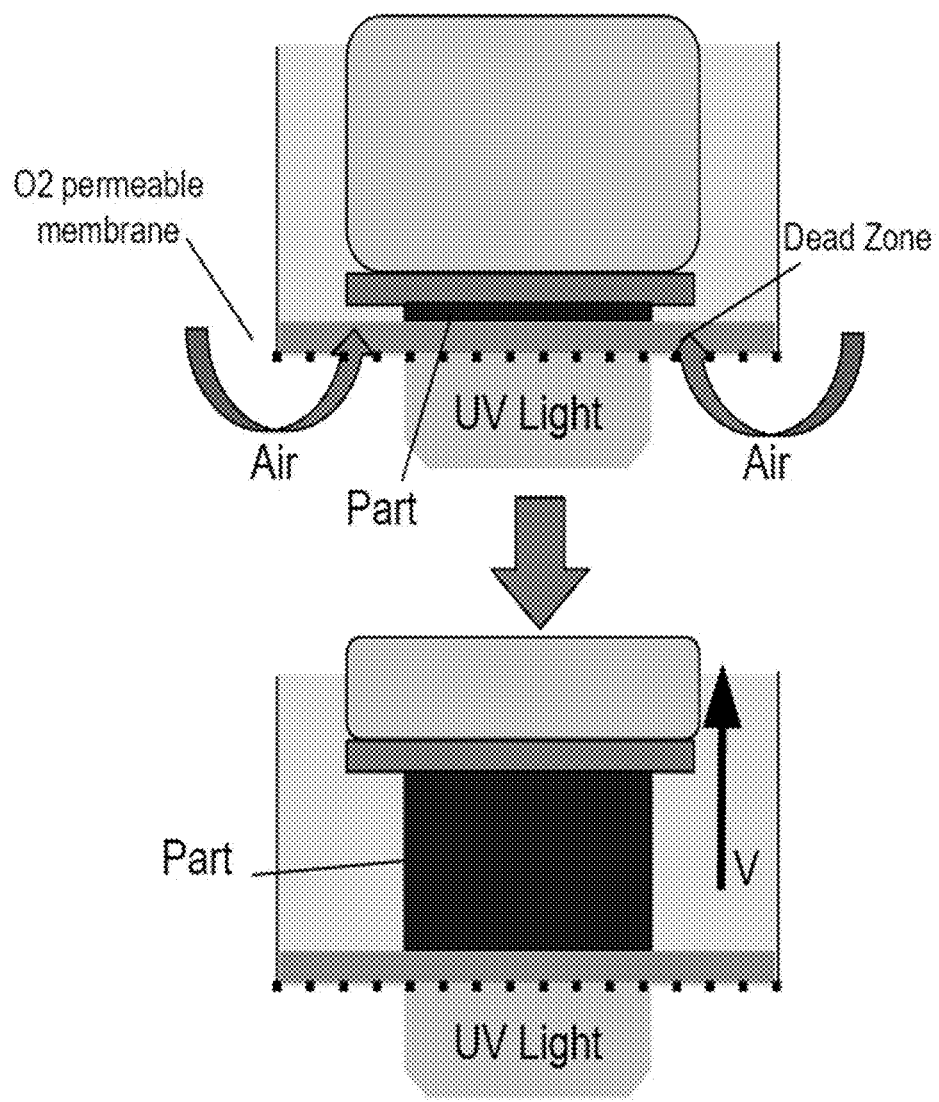
FIG. 8. Micro-CLIP printing system schematic. UV light is projected through a thin oxygen permeable membrane. Liquid polymer material solidifies in the pattern projected and the build platform raises vertically out of the liquid material bath.

An exemplary process flow is depicted in FIG. 7. Prior to fabrication, a photo-curable biomaterial ink was formulated as described in the section below. The CAD structure is sliced into a series bitmap images using a MATLAB code developed specifically for this system. The UV absorber and light intensity concentration is tuned to obtain a curing depth of 20 microns, determining the necessary slicing layer thickness.

The silicon wafer is then aligned with the top of the biomaterial ink layer, and the 160 liter PµSL chamber is filled with nitrogen gas. This reduces the concentration of oxygen within the chamber and ensures optimal solidification and resolution of the photo-curable biomaterial ink. Afterwards, the layer building process begins. The first sliced bitmap image is displayed on the dynamic mask (in this case, a 1400×1050 pixel array), and the wafer drops by 20 microns. The system then waits for 30 seconds for the biomaterial ink to settle. The UV lamp is turned on for 20 seconds, reflects off a beam splitting mirror, passes through a reduction lens and finally projects onto the surface of the biomaterial ink in high resolution, with each pixel corresponding to 7.1×7.1 µm² repeats for each bitmap layer in the fabrication. The micro-structure is then removed from the PµSL machine, cleaned with isopropyl alcohol (IPA), dried under a low flow rate nitrogen gun. At this point, the biomaterial ink within the structure has not completely solidified. To finish the curing process and bring the biomaterial ink to its final state, the structure is further exposed to UV for post-curing.

Stent Design

Stent design with various microstructures were prepared using the SOLIDWORKS CAD software (Waltham, Mass.). Sinusoidal formed wire, helix wrap and meshed tube was created and printed along the circumference layer-by-layer with length×outer diameter×thickness. Various parameters such as 300 um, 350 um, 400 um and 500 um in thickness or 9.0 mm, 16 mm and 21 mm in length were investigated. Typically, a stent pattern was chosen to be a triangular truss structure along the circumference with each new row connected via vertical supporting rods, as shown in FIG. 3a. Each new row was shifted to allow the lowest point of the upper row to be in line with the highest point of the bottom row. These points were then connected by vertical beams that gives the appearance of hexagonal holes across the face of the cylinder. To avoid misalignment and a floating point at the low point of the top row, vertical support rods were placed at low and high point section for fabrication.

The rods with smaller cross section act as removable support structure that were removed after fabrication was completed, outer diameter of stent was given a set value of 5.20 mm Stent strut thickness was set to 350 um, the individual "true support" stent rod diameter was also set at 350 um and a height of 550 um tall. The "removable support" material rods were set to a value of 100 um with a height of 300 um. Further support rods of 150 um diameter and 300 um tall were placed at the bottom of the stent to allow easy removal from the base. The entire stent was built on a square base of 5.5 mm×5.5 mm by 500 um tall. This overall design was initially chosen in order to verify the capability of the PμSL system to manufacture such structures as stents. Optimization to this design and other design changes was performed.

Morphological Assessment of the Stents

Samples of printed stents were observed in high vacuum mode (<10-4 Torr) with 10 kV operation voltage by utilizing FEI Quanta environmental scanning electron microscopy (ESEM) without polish and coating.

Mechanical Testing

Mechanical compressive tests of mPDC stents were conducted according to ASTM D2412-11 by parallel-plate loading on an Instron 5544 mechanical tester equipped with 500N load cell at a rate of 100 mm/min (Instron, Canton, Mass.). Radial compression testing was performed by compressing mPDC stents a total of 2 mm corresponding to 33% to 50% displacement depending on stent outer diameter. A three-point bend test apparatus (a cylindrical actuator in the middle of two cylindrical end-supports at a distance of 20 mm) was used for flexibility testing, which was performed according to ASTM F2606-08 on a MTS Sintech 20/G Universal Testing Machine with 210 N load cell at a crosshead rate of 10 mm/min (Sinotech, Portland, Oreg.). The maximum bending angle was set at 48°.

Numerical Simulation

Numerical simulation for three-point bending and parallel-plate compression of stents were performed utilizing the SOLIDWORKS (Waltham, Mass.) and ANSYS workbench (Cecil Township, Pa.) softwares. Three thicknesses of 300 um, 350 um, and 400 um and length of 21 mm of stents were examined for both the parallel-plate compression and three-point bending simulations. To simulate 3-point bending, the stent was fixed on one side and two regions near the edges while forces were added along half the length of the stent, the displacement field was analyzed. In the parallel-plate compression, the forces were applied in a slim region along the length of stent.

Polymer Synthesis and Characterization

Citric acid is a multifunctional monomer in the Kreb's cycle that is easily reacted with various diols to form a crosslink elastomer in the absence of exogenous catalysts (ref. 26; incorporated by reference in its entirety). Under a controllable condition and procedure, the synthesized PDDC prepolymer was uncrosslinked and was dissolvable in several solvents such as ethanol, acetone, dioxane, etc. (ref.28; incorporated by reference in its entirety). In basic conditions, glycidyl methacrylate was used in an epoxide ring-opening reaction to attack the unreacted carboxylic groups of citric acid using imidazole as a catalyst. Methacrylate was successfully introduced to the PDDC backbone. A novel mPDC polymer was obtained as determined by $^1$H NMR spectrum with evidence of proton peaks for citrate residues (1) and methacrylate residues (5 and 6) (FIG. 1). The multiple peaks at 2.79 ppm were assigned to the protons in —CH2— from citric acid, and the peak at 1.84 ppm was assigned to —CH3 in methacrylate unit. The molar composition of mPDC calculated from the signal intensities of both protons was approximately 1:1 of citric acid/methacrylate. mPDC polymer immediately forms a solid by photopolymerization after mixing with a photoinitiator as shown in FIG. 1.

Figure 2:
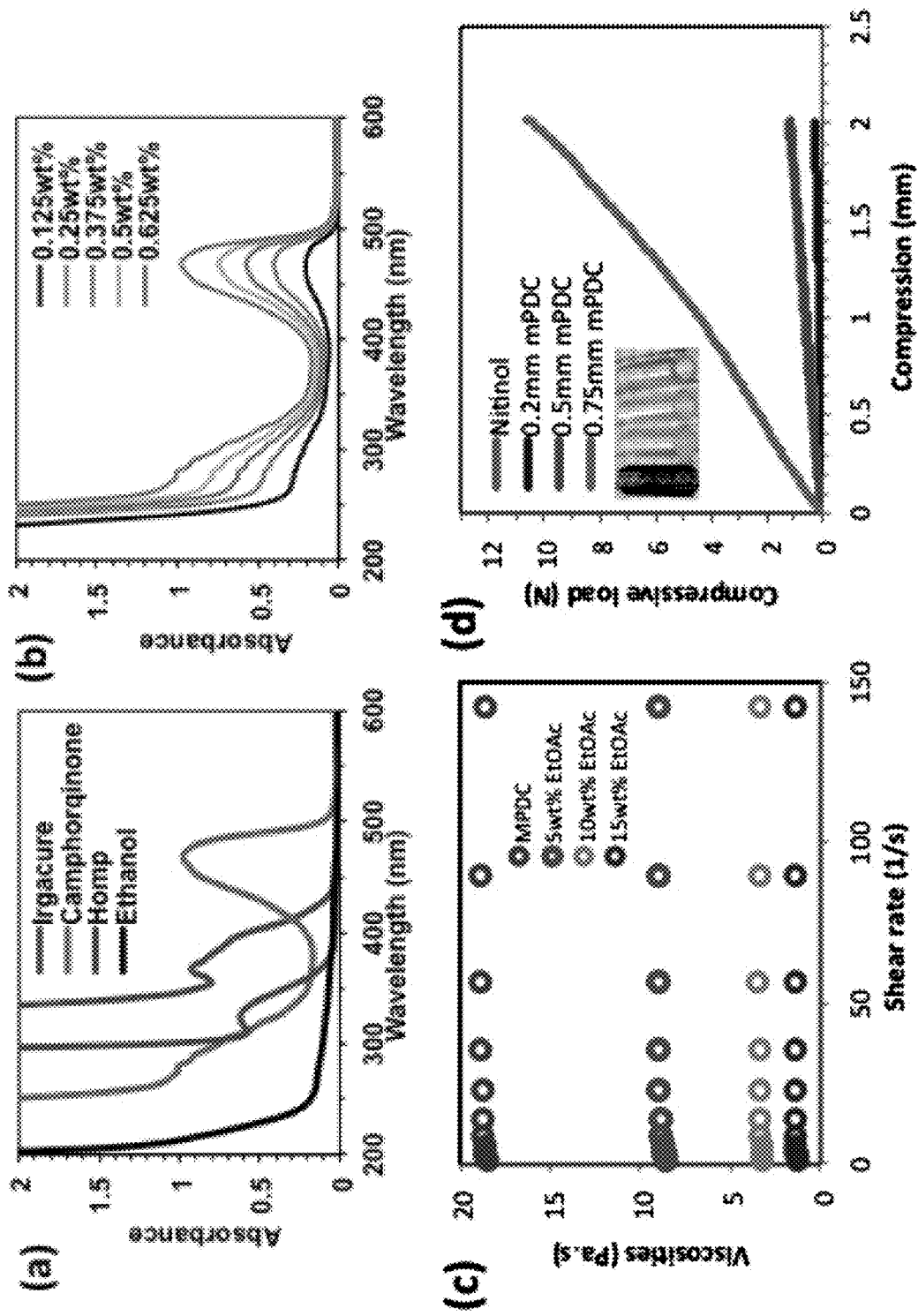
FIG. 2. (a) UV/Vis absorption spectra of Irgacure 819, Camphorquinone and 2-hydroxy-2-methylpropiophone (Homp) in ethanol; (b) UV/Vis absorption spectra of Camphorquinone at different concentrations; (c) Dynamic viscosities of methacrylated methacrylated poly(1,12-dodecanediol citrate) (mPDC) polymer solutions with different amount of ethyl acetate; (d) Compression strength of in-situ mPDC stents of different thicknesses, the stent is 21.8 mm×5.0 mm (length×outer diameter).

Biomaterial Ink Formulation and Rheological Characterization mPDC polymer is easily dispersed and formulated in different chemicals such as ethanol, acetone, dioxane, ethyl acetate, 1-butanol, Diethyl adipate, 1,6-hexanediol diacrylate and Diethyl fumarate, etc. mPDC viscosities do not change significantly in a shear rate from 1 to 150 l/s, at 15.5±0.4 Pa·s as shown in FIG. 2c. Upon adding different amounts of ethyl acetate, the mPDC solution remains flowing stable, the viscosities remarkably decrease over shear rate with the increasing ethyl acetate, from 8.0±0.5 Pa·s in 5 wt % to 1.50±0.04 Pa·s in 15 wt %. However, all the viscosities of the polymer and solution decrease over temperature, heating can increase the flowability of both polymer and solution.

It was observed in the experiments conducted during development of embodiments herein that all the initiators, co-initiators, and free radical quenchers are easily dissolved in the mPDC solution forming a homogenous solution and quickly forming a solid upon exposure to light. FIG. 2a showed the UV/Vis absorption of different initiators such as Irgacure 819, Camphorquinone and 2-hydroxy-2-methyl-propiophone separately in 370 nm, 470 nm and 340 nm, with the concentration dependence. After being cured with Camphorquinone at 470 nm, the mPDC stent in 0.5 mm thickness showed complete compliance with BMS in compressive strength in FIG. 2d, compressive modulus of mPDC stent in 0.75 mm increased to 10.64±3.6 MPa. Similarly, to increase the resolution of projection microstereolithography printing, 2.2 wt % Irgacure 819 was used as the photoinitiator and 0.18-0.22 wt % Sudan 1 as the UV absorber after a series of optimization. Irgacure 819 can easily bind both HDDA and mPDC independently at a molecular level, while Sudan I absorbs UV light at 405 nm provided by the printer to control the curing depth.

Projection Microstereolithography Printer Design and Fabrication

Projection microstereolithography printer design was based on digital micromirror device (DMD, Texas Instrument) as a dynamic mask at 1400×1050 pixels that is the core of this technique to use a spatial light modulator. The modulated light was transferred through a reduction lens (CoastalOpt 60 mm UV-VIS-NIR lens, JENOPTIK Optical System Inc.) to the surface of biomaterial ink with the reduced feature sizes, each pixel in the dynamic mask is focused down from original dimensions (object size) of 10 um×10 um to an image size of 7.1 um×7.1 um, the magnification is approximately 1.4. The biomaterial ink can be cured at a 2D pattern in a single exposure and stacked in a series of closely spaced horizontal planes programmed by a 3D CAD model. In the projection microstereolithography printer, the intensity of UV light is controlled by the current input into the system with 0.4 A at 405 nm, the measured intensity is 0.03 mW. Typically, the curing time for HDDA stent is 12 seconds per layer and 20 seconds per layer for mPDC stent. With this bottom-to-top fabrication, the biomaterial ink enables printing the stents with high resolution of 7 um pixel in a curing depth of 20 um. The cured biomaterial ink has strong enough mechanical properties to enable 350-400 um struts over a 21 mm stent design height, as shown in FIG. 3c-d and FIG. 4, each layer is 20 um in depth with precise edges.

Morphological Assessment of the Stents

Figure 3:
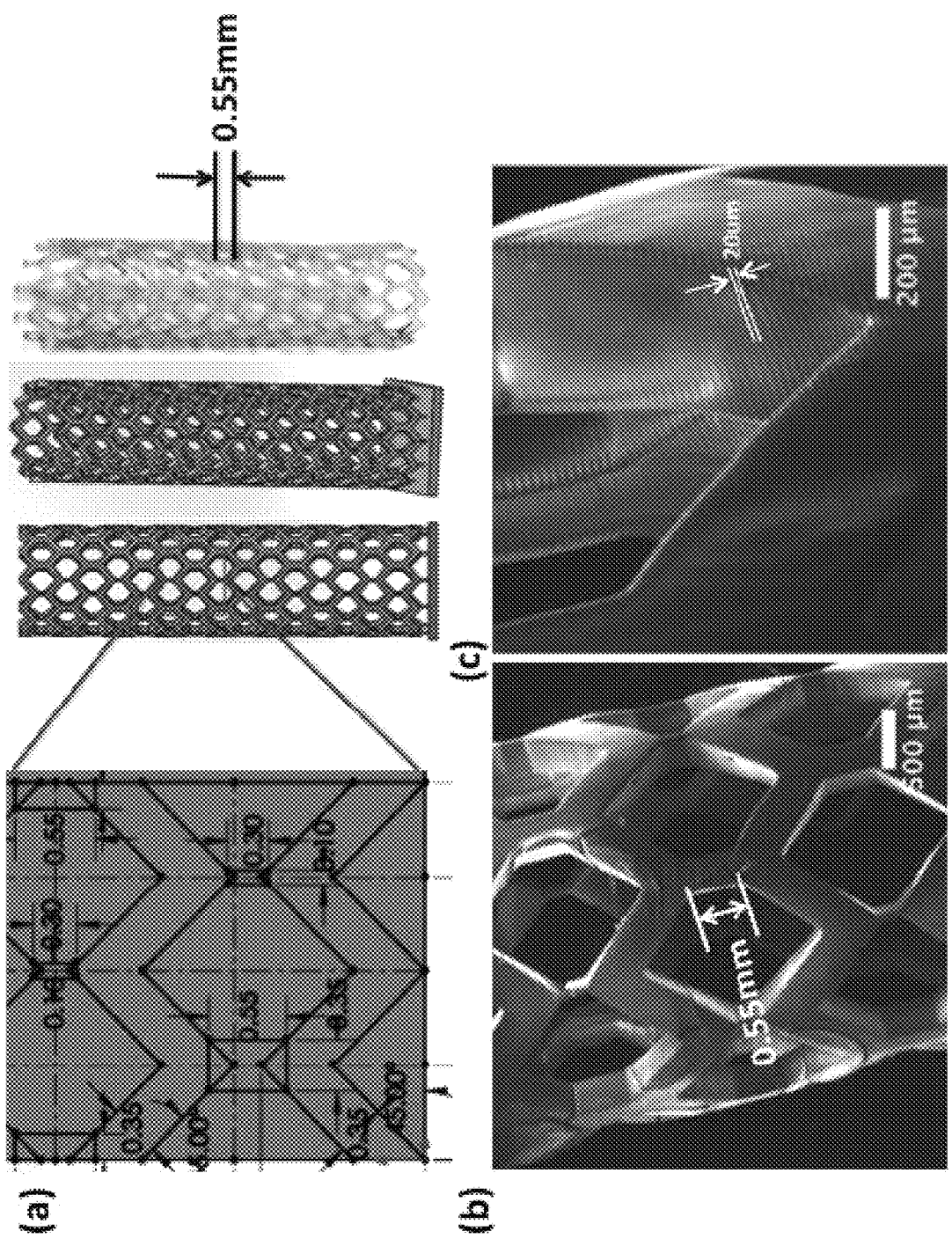
FIG. 3. (a) Sketch and gross image of typical repeating stent element and full 3D CAD Design of the stent; (b & c) Scanning electron microscopy images of a printed mPDC stent showing the 20 um layers.
Figure 4:
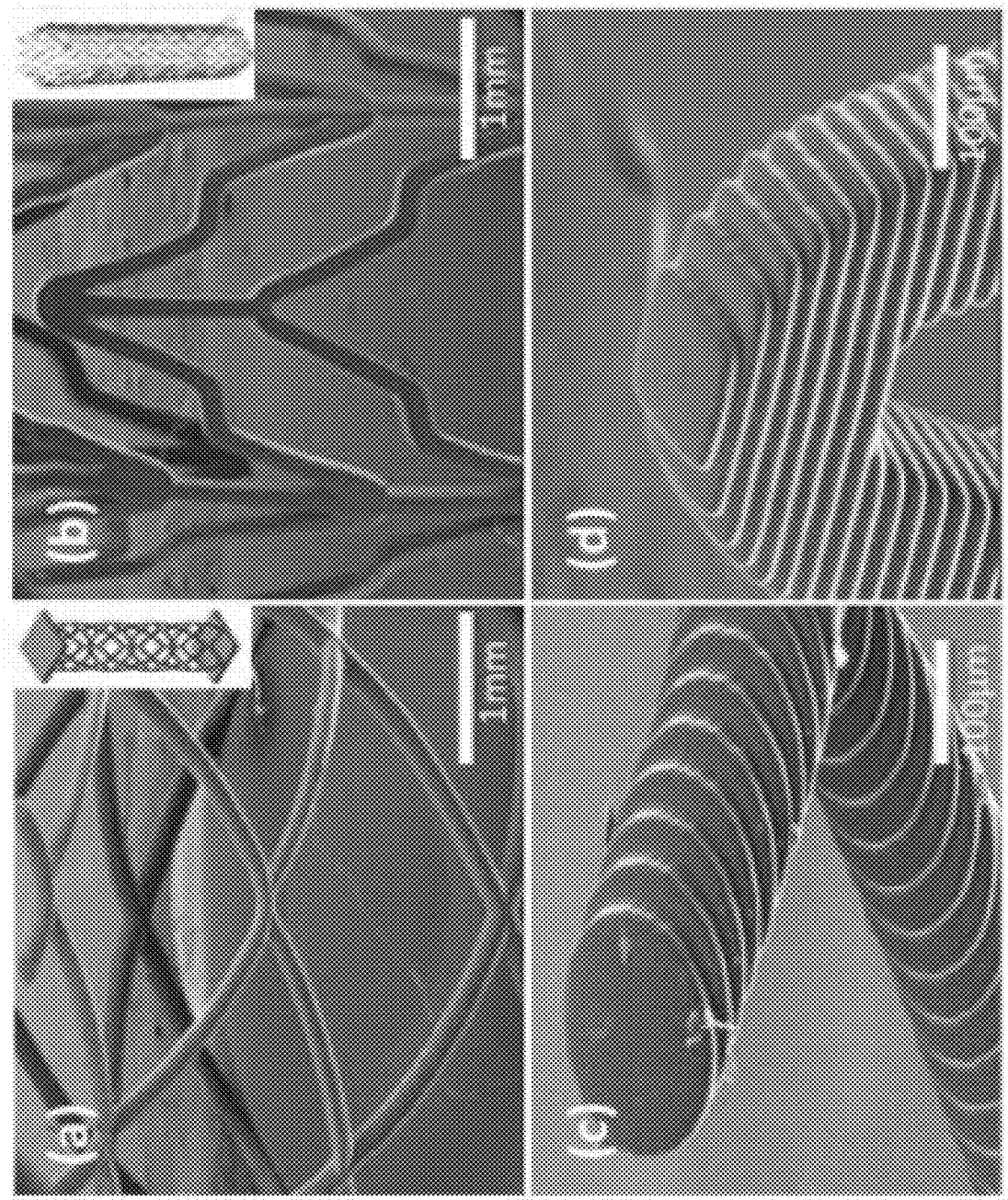
FIG. 4. (a & c) Low and high magnification of SEM images of a mesh mPDC-HDDA stent, CAD design shown in the top right corner; (b & d) low and high magnification of SEM images of sinusoidal an mPDC-HDDA stent. CAD design shown in the top right corner.

In this process of bottom-to-top microfabrication, various microstructures in the stents were also showed in FIG. 3c-d and FIG. 4. Sinusoidal wire and fiber mesh were stacked in circular and rectangular layers with 20 um height. In FIG. 3, SEM images showed sinusoidal stent was interconnected with bridges in 0.55 mm as designed as vertical support rods. Experiments conducted during development of embodiments herein demonstrate that projection microstereolithography can print the stents with various microstructures.

Mechanical Testing

Figure 6:
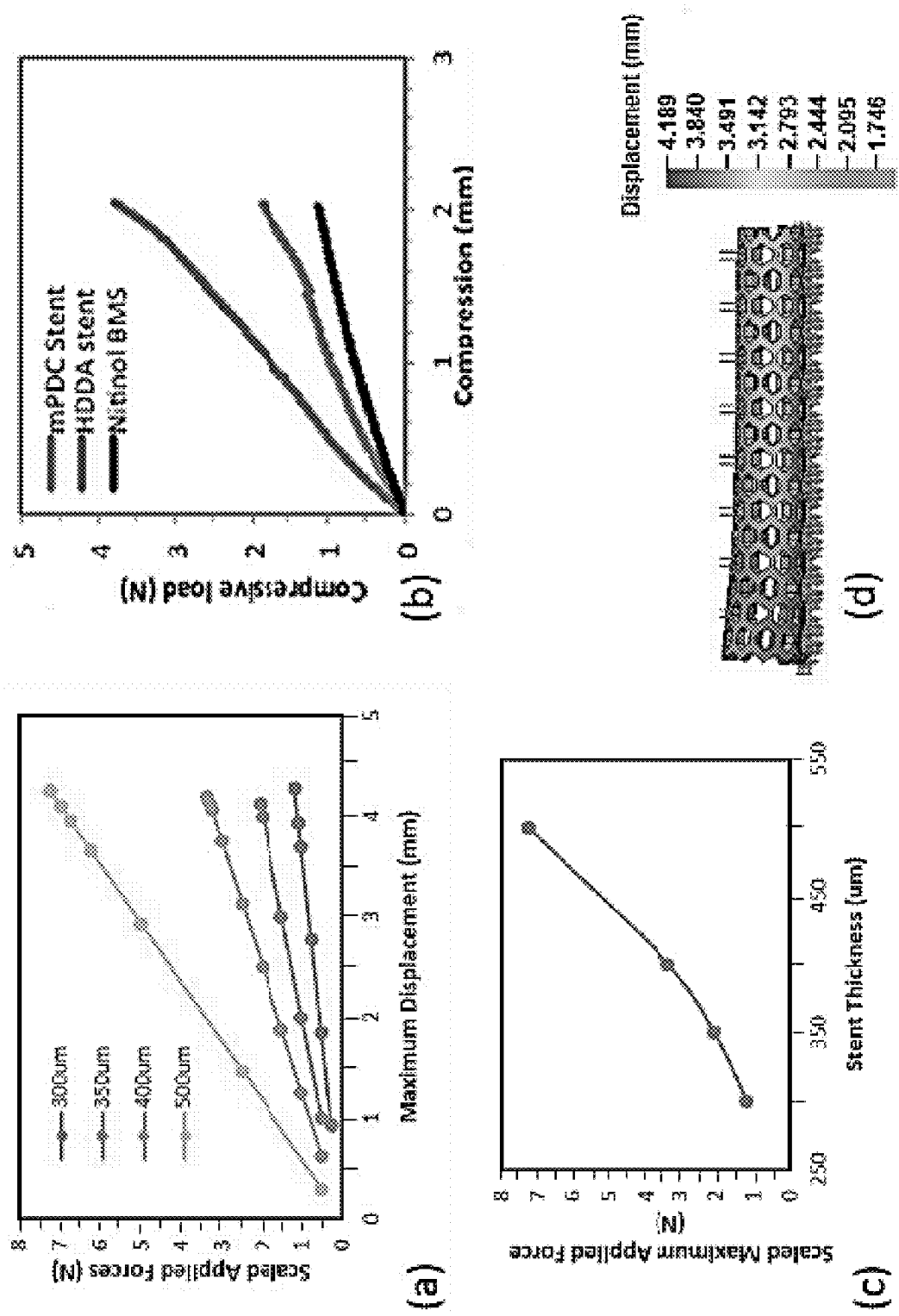
FIG. 6. (a) Scaled Applied Force vs. Maximum Displacement profile of stents with 300 um, 350 um, 400 um and 500 um in thickness. (b) Compressive strength of Nitinol BMS (21.8 mm×5.0 mm×0.2 mm), HDDA and mPDC printed stents with 9.1 mm×5.5 mm in length×outer diameter, the thickness of printed stent is 500 um; (c) Scaled Maximum Usable Applied Force vs. Stent Thickness curve; (d) Typical Displacement distribution for Parallel-Plate Compression simulation of stent with 400 um in thickness.

Parallel-plate compression and 3-point bending experiments were performed to determine the mechanical properties of stents. Unlike in-situ mPDC tubes, the mechanical properties of printed stent are significantly affected by stent design and its microstructure. mPDC significantly change HDDA compression strength and make it more flexible to match Nitinol BMS, as shown in FIG. 6b. By compressing 2 mm from 5.5 mm in outer diameter, no complete rupture was found so that this closed microstructure resists the mechanical fracture of stent.

Numerical Simulation of the Stent Design

Figure 5:
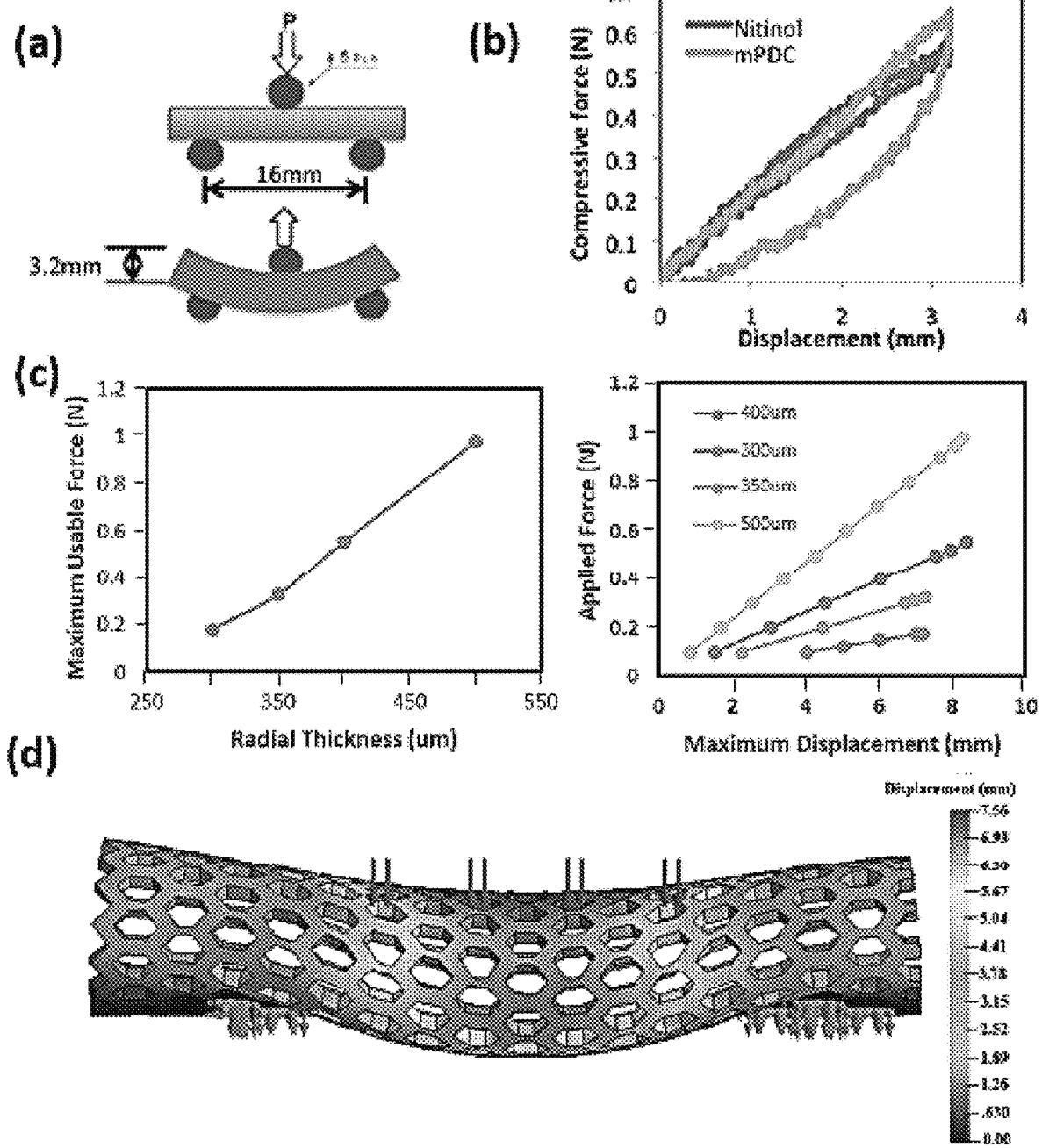
FIG. 5. (a) Schematic view of 3-point bending experiment with a gap of 16 mm and compressive displacement of 3.2 mm for stent with 5 mm outer diameter; (b) compressive displacement and resilience of Nitinol (21.8 mm×5.0 mm×0.2 mm) and mPDC stent (21.8 mm×5.0 mm×0.5 mm, (length×outer diameter×thickness)); (c) Simulated maximum force-displacement curves for different thickness stents and force-thickness curve at onset of kinking in 3-point bending simulation; (d) Simulated loading and displacement field for 350 um stent in 3-point bending simulation.

To accomplish the simulation for three-point bending, on one half of the stent circumference, two regions near the edges of the stent were fixed, while forces were added along half the length of the stent on the opposite side of the fixed area. A typical displacement field from a 400 um thick stent is presented in FIG. 5d. From an applied force of 0.5N onto the 400 um stent, the resulting maximum displacement of 7.945 mm was observed where forces were applied. The displacement on the opposite end of the stent was 3.783 mm. For all three stent thicknesses, the maximum displacement was plotted against the force applied to the stent (FIG. 5c). For increasing stent thickness, the necessary applied force to displace the stent increases. The primary properties analyzed in these simulations were the range of forces that these stents are predicted to be usable. The stent was considered "unusable" when the point of maximum displacement is within 1 mm from the point on the opposite side of the circumference of the stent. This was determined from the following equation:

$$(Dd+d2)-d1;$$

where Dd is the outside diameter or the stent, d2 is the displacement of the point opposite the point of maximum displacement, d1 is the maximum displacement value. With increasing thickness (μm), the Applied Force necessary to make the stent unusable increased (FIG. 5d). These Applied Force values for the 300 um, 350 um, and 400 um thick stents were 0.18N, 0.325N, and 0.555N, respectively.

The parallel-plate compression was simulated on the three stent designs. With increasing force, there is nonlinear contact between the plates and the new deformed surface of cylinder. The parallel-plate compression analysis was done for this study by fixing a slim region along the length of the cylinder be fixed. Particular faces on the cylinder's opposite side were subjected to equal forces. As with three-point bending, the range of forces that the stents were "usable" were analyzed (FIG. 6a) and the Maximum Usable Applied Force was plotted in relation to stent wall thickness (FIG. 6b). With increasing stent thickness, the necessary force to cause deformation of the stent walls increased. The numerical results and the experimental results differed by approximately a factor of 5. A scaling factor of 5 was used in order to compare the experimental results and the numerical results. FIGS. 6a and 6c represent Applied Forces multiplied by the scaling factor.

With the scaling, the numerical simulation becomes more directly comparable to the experimental tests. The "HDDA" stent used for the experimental tests was a design that was 500 um in thickness for both the stent walls and all supporting rods. This slightly differs from the design that is numerically evaluated. The design that is being evaluated numerically has some support structures of (100 um). At 2 mm compression, the HDDA stent needed approximately 4N of applied force to cause displacement. At 2 mm of compression, the 500 um design needed approximately 3.5N of force. This difference could be attributed to the inclusion of smaller 100 um support rods. The 350 um stent best approximates the Nitinol BMS stent. In both cases, approximately IN of force is necessary to compress the structure 2 mm.

Example 2

Micro-CLIP Additive Manufacturing Process

Design, Print Custom Design, Tailor Performance

Using the exemplary manufacturing process described below, 7.1 um lateral resolution was obtained. The combination of manufacturing process, material, and design flexibility allow for the custom fabrication of stents to fit the needs of a particular subject or application.

Micro-CLIP manufacturing method is based on a similar methodology as Projection Micro-Stereolithography. In some embodiments, the Micro-CLIP system is capable of printing up to 200 times faster than projection stereolithography method.

With a single Micro-CLIP printer devices were generated at the necessary scale for low-volume manufacturing. When using projection stereolithography (PuSL), 16 hours of time were required for a single print. With Micro-CLIP a new 20 mm length stent can be printed in just five minutes. By Micro-CLIP, the slowest prints tested took only seventy minutes, which is nearly 15 times faster than the PuSL system for a high resolution object of 1000 layers. This time is further reducible through the use of properly optimized material, light source, and dead zone. This technology has additional advantages including the ability to work with a broader array of polymer materials and each print has isotropic material properties. However, compared to PμSL, Micro-CLIP has weaker provided mechanical properties under compression. With PμSL, the maximum stent length possible was 20 mm With Micro-CLIP, the maximum stent length achieved is 48 mm, with significantly greater length achievable. Devices much taller than 200 mm are achievable with this technology depending upon the materials used and the structure to be printed.

Micro-CLIP additive manufacturing provides for the fabrication of microstructures from a photo-curable biomaterial ink in a layer-by-layer fashion directly from a 3D CAD design. Each layer is cured in a single exposure using a digital micromirror-device (DMD) as the dynamic mask for the UV light. This differs from the PμSL system which uses a liquid crystal display. The liquid crystal display is not able to withstand the high power UV required for the Micro-CLIP process. This allows for a dramatic reduction in fabrication time compared with conventional 3D printing processes, which fabricate 3D structures in a point-by-point scanning fashion. In addition to fabrication of an entire surface area at once, CLIP operates under nearly continuous motion. In a PμSL process, after the first layer forms, the fabricated part is typically dipped back into the liquid resin bath and then raised so that only a single ~5-20 um layer of liquid is on top of the part, then time is allowed for the material to settle, a process that can take 30 seconds to two minutes per layer depending on the material viscosity. That entire process is eliminated in CLIP. With CLIP, the platform moves upwards at a nearly constant speed, only stopping for 10 ms-100 ms between each layer, dramatically reducing part print speed. Additionally, a higher intensity of UV light is used which enables photocuring each layer of the part in dramatically less time.

CLIP Process Flow

Prior to device (e.g., stent) fabrication, a photo-curable biomaterial ink was formulated as described in the section below. The CAD structure is sliced into a series of bitmap images using a MATLAB code developed specifically for this system. The UV absorber and light intensity concentration were tuned to obtain a curing depth of 20 microns to tune the finalized surface finish of the part. During the alignment process the Teflon AF2400 thin film was aligned to be placed 20 um below the focal plane of UV intensity. During the print process the build platform then drops down until it comes in contact with the Teflon AF2400 thin film, contact is determined via a force sensor built into the platform. The purpose of the Teflon AF2400 thin film is to control the oxygen flow rate that makes contact with the liquid resin. Oxygen inhibits the photo-polymerization reaction and by allowing just a small amount into the bath a dead-zone forms. The printing process then begins and the first sliced image is displayed on the digital micromirror devices (in this case a 1980×1050 pixel array). The system begins moving upwards at the desired user controlled speed (80 um/s for example) until the system has moved upwards 20 um. The system then briefly stops, switches images to the second sliced image, waits for 10-100 ms to ensure a full switch of the image, and then begins moving again at the user controlled speed. Speed, UV intensity, and image are dynamically controllable and modulatable at each individual layer of the print. Layer thickness does not have to be 20 um, it can be as low as 100 nm. This process continues, with the platform continuing to move up and new images continuing to be displayed until the entire part is completed.

In terms of the light path when the UV LED is turned on, the light first passes through a collimating lens, through a light gate and then reflects off a digital micro-mirror device which contains millions of tiny mirrors. The reflected light passes back through the light gate, through a focusing lens and beam-splitter and off a 90 degree mirror before ending at the focal plane with each pixel corresponding to 7.2×7.2 um^2.

After the part was complete, the micro-structure was then removed from the machine, excess material was cleaned off with a chem-wipe and the part was left in a dionized water bath for a few hours to remove any excess material. To improve mechanical strength the parts were then removed from the water bath, dried under a nitrogen gun and post-cured under an intensity of 350 mW/cm$^2$ for 6 minutes (3 minutes on each side).

Resolution Accuracy

Figure 10:
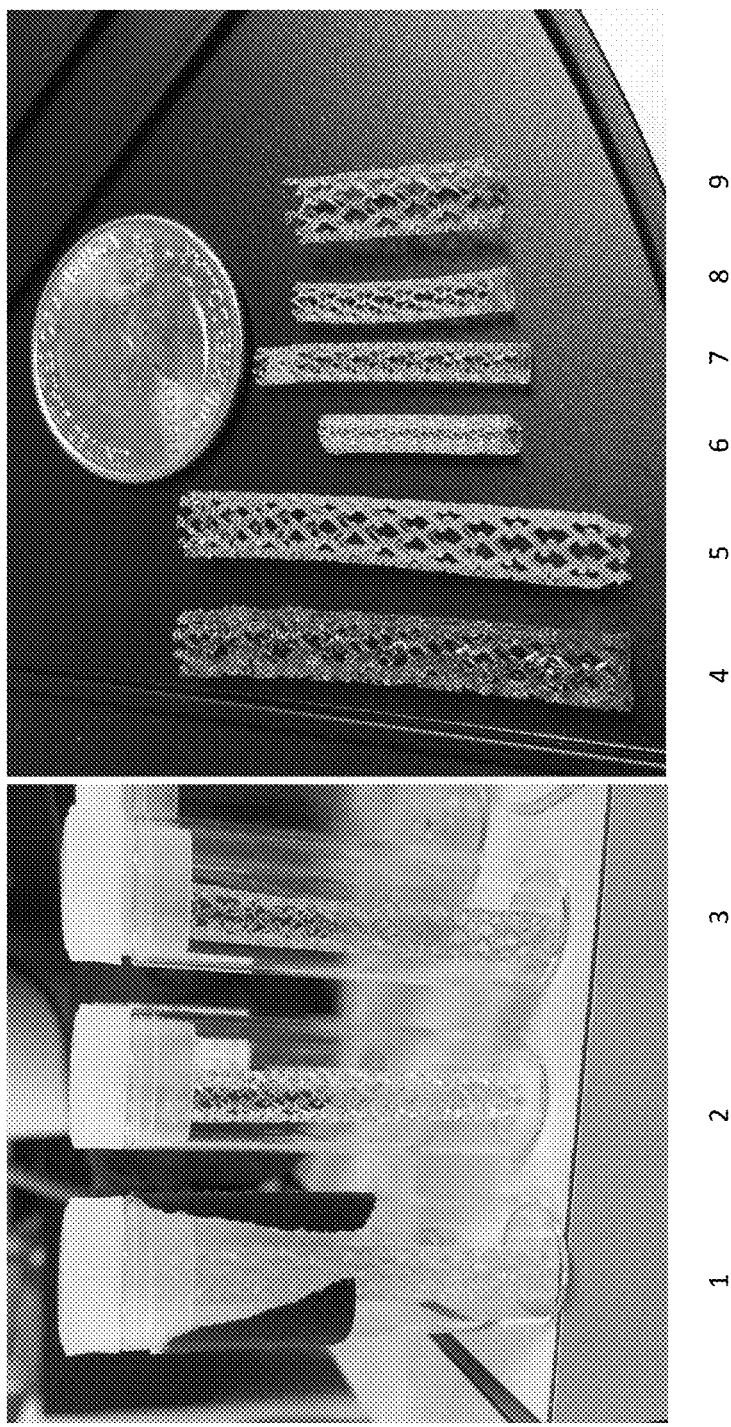
FIG. 10. Stents Printed with various materials and how that impacts their aesthetics. Stent #1: 47.79% mPDC, 50% DEF, 0.01% Sudan I, 2.2% Irg 819. Stent #2: 97.78% HDDA, 0.02% Benzotriazol, 2.2% Irg 819 Stent #3: 97.79% HDDA, 0.01% Sudan I, 2.2% Irg 819. Stent #4: 80% mPDC, 17% DEF, 2.2% Irg 819, 0.1% Sudan I. Stent #5: 50% DEF, 47.79% mPDC, 0.01% Sudan I, 2.2% Irgacure 819. Stent #6: 50% mPDC, 47.79% DEF, 2.2% Irgacure 819, 0.01% Benzotriazol. Stents #7-9: 60% mPDC, 35.58% Ethanol, 4.4% Irgacure 651, 0.02% Benzotriazol.

Resolution of the fabrication systems is affected by several variables from both the fabrication system and the fabrication material. Potential variables include the following: speed of fabrication, light intensity, amount of pause at each fabrication layer (exposure time), concentration of UV absorber in material, and concentration of photoinitiator in the material. Several fabrication tests were performed that varied several of the parameters listed above. Shown in FIG. 10 are the dimensional differential vs. light intensity plots from four tests that were performed. For these tests, the fabricated dimensions of the stents were compared against the intended stent design dimensions. "Base" stent design has an intended dimension of 151.4 um strut thickness in the axial and lateral (planar) directions. Dimensional differential is the percentage difference between the actual fabricated dimension and the intended dimension. Values below the X-axis represent the fabricated dimension is a certain percentage smaller than intended (underexposure) and values above the X-axis representing the fabricated dimension being a certain percentage larger than intended (overexposure). The X-axis represents fully accurate dimension resolution (correct exposure). Light intensity was measured as the percentage of the system's maximum intensity. Photoinitiator and UV absorber used in these tests were Irgacure 819 and Sudan 1, respectively. Exposure time (pause of machine at each fabrication layer) was either 1 ms or 10 ms. Fabrication speed was fixed at 5 um/s. Fabricated dimensions were acquired from scanning electron microscopy and imageJ software and represent an average along the length of the stent. From these tests areas where accurate resolution could be achieved were identified for each material.

Figure 9:
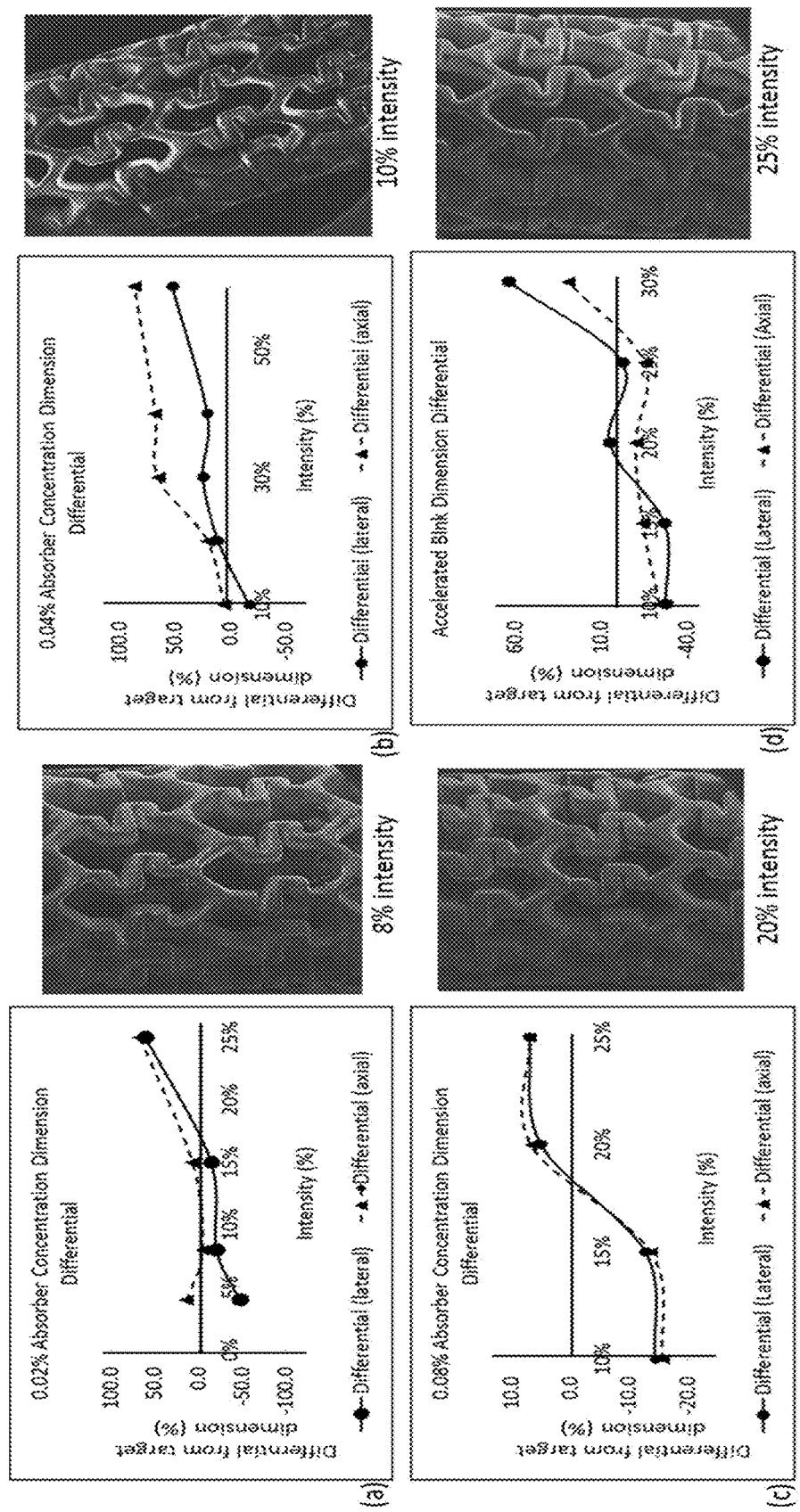
FIG. 9. Dimensional Differential vs Light Intensity (% of max). Beside each plot is the corresponding SEM micrograph of the closest experimentally tested value to dimensional accuracy.

FIG. 9(a) represents a test with a biomaterial ink resin containing 2.2% photoinitiator, and 0.02% absorber concentrations. The exposure time for this set of stents was 1 ms. From this test it was observed that the correct axial exposure was achieved at approximately 13% or 14% intensity. Correct lateral exposure was achieved at 17-18% light intensity. FIG. 9(b) represents a test with the absorber concentration increased to 0.04% and exposure time increased to 10 ms. At 10% light intensity, axial differential was only approximately 5%, a decrease to 8% or 9% light intensity could potentially be give dimensional accuracy. Correct lateral exposure appears to be achievable at 15% light intensity. In the test represented by FIG. 9(c), the absorber was increased to 0.08% concentration, with other variables unchanged. Lateral and axial differentials are very similar in this test. Both axial and lateral dimensional accuracy appears to be best at approximately 17-18%. In the last test, FIG. 9(d), initiator was reduced to 1% concentration and a polymerization accelerant was added [ethyl 4-(dimethylamino)benzoate] at 1% concentration. Lateral correct exposure was achievable at approximately 19% or 22-23% intensity. Correct axial exposure was achieved at approximately 26-27% intensity. In this last case, the stents appear to laterally overexpose at lower light intensity than in the axial direction. For cases where there is overexposure in the axial direction at lower intensity than the lateral direction, more pixels could be added to each projected cross section to make all directions dimensionally accurate. In the case where the lateral direction experiences overexposure at lower intensity than the axial direction, a reduction in projected cross section pixels compensates for lateral overexposure.

Material Flexibility:

A broad variety of liquid polymer materials function well within these additive manufacturing processes. Solvents including Ethanol and Ethyl Acetate have been used to replace Diethyl Fumarate in the material composition of each individual stent. Because Ethanol has a lower viscosity than Diethyl fumarate, less Ethanol is necessary within the final material to match the viscosity requirements for printing. Ethanol and/or Ethyl Acetate improve the biocompatibility of the process. In addition to changing the solvent used, the UV Absorber, Sudan I can be changed to Benzotriazol, a UV absorber that is nearly transparent in the visible spectrum and causes the printed object to look clear to the human eye. A large variety of photo-initiators are compatible with this process including but not limited to Irgacure 819, Irgacure 651, Irgacure 369, Irgacure 184, Irgacure 2959, Irgacure 1173, 2-hydroxy-2-methylpropiophone (Homp) and Camphorquinone. Transparent materials are being used to create a look of cleanliness for both the surgeon and the patient and improve the aesthetic quality of the device.

Design Flexibility

Figure 11:
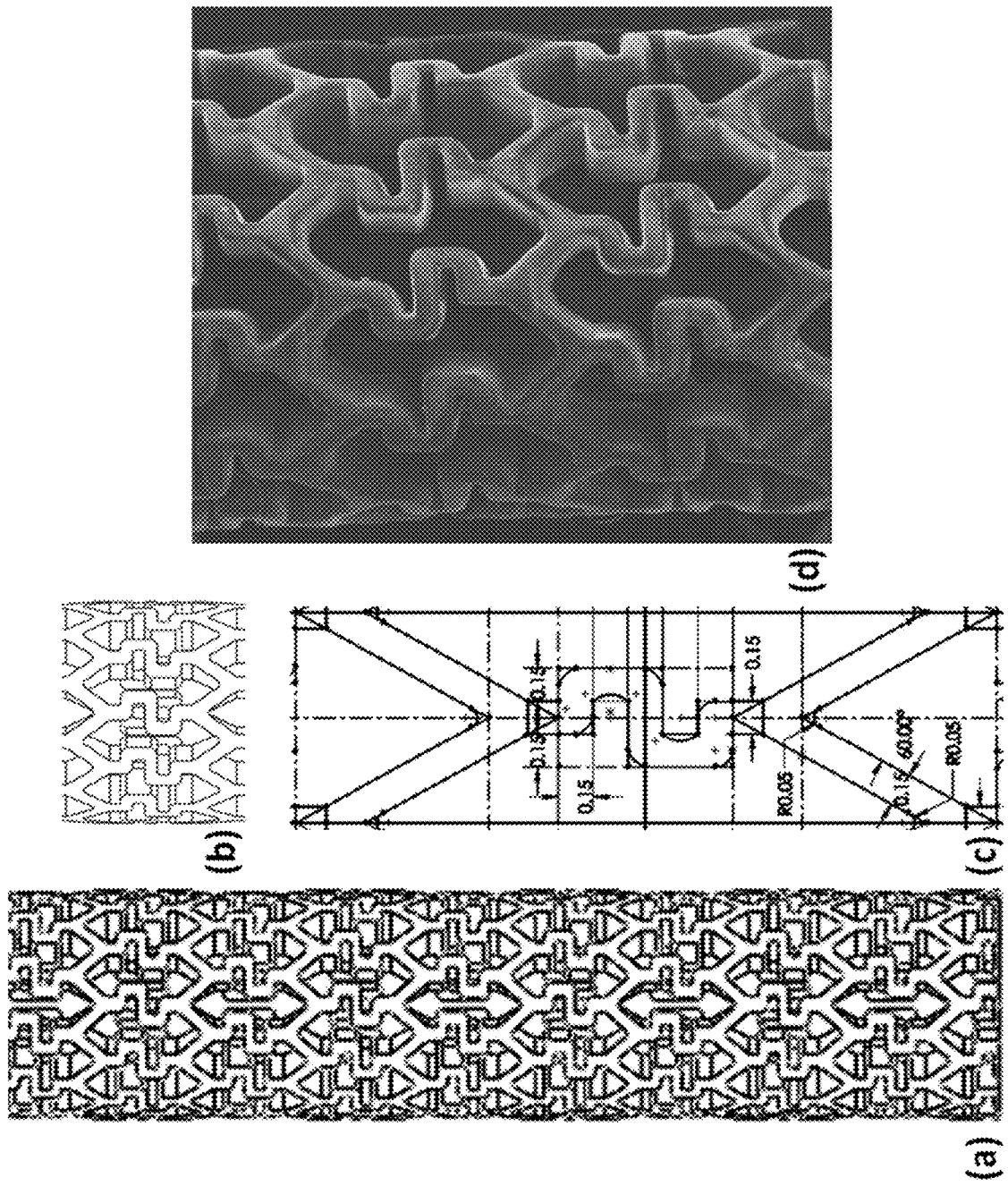
FIG. 11. Base Design: (a) CAD Drawing of full length stent. (b) CAD drawing of unit length of stent. (c) Unit Cell Design. (d) Scanning electron micrograph of design from CLIP process.

AM processes allow for excellent design flexibility and tunability. With both PµSL and CLIP processes a base stent design can be experimentally tested and quick design iterations are possible. The ability to free form fabricate structures with very high resolution within the span of at most a few hours (PµSL) to as low as a few minutes (CLIP) allows for very fast direct experimental testing and design iteration. Depending on the patient's needs, such as size and location of lesion within the vessel or vessel geometry, these manufacturing processes accommodate changes in a base stent design to a complete custom design. If large radial strength is needed, wall and strut thicknesses are editable. If more flexibility is needed, strut connector design is edited. Instead of having a standard set of sizes for vascular diameter, AM processes allow for a specially made stent to fit the particular vessel. While AM processes have certain advantages in terms of flexibility compared to other manufacturing processes, AM processes still have their own requirements. For stereolithography based manufacturing (scanning, projection, CLIP), each fabrication layer must be connected to a previous fabrication layer, a support fabrication post, or the build platform. If a design does not account for this requirement, the printed structure will have structural defects. To accommodate this requirement, current stent designs have the low point of each strut ring connected to some portion of the connector ring below it. Two designs that have been created and parallel-plate compression tested. Our "Base" design shown in FIG. 11 below and Arrowhead design in FIG. 12 have been compression tested, while the Flexibility Optimized Base design (FIG. 14) is a conceptual design that has not been mechanically tested yet. The Base design was created to be closely packed to increase radial strength, while the "S" shaped connections were added to provide reasonable flexibility. For validation of mechanical properties, a base design was made similar to a design on the market. Designs made for patients can be tailored to suit the patient's needs. A unit length of the "Base" stent design consists of 12 unit cell elements across the circumference of the stent. This unit length of the stent could then be added to one another until the desired full length was obtained. Strut thickness of the Base design was set to be 151.4 um. The angle between struts was set to be 60 degrees. Lastly, the stent wall was given a thickness of 500 um for the bulk of mechanical testing.

Figure 12:
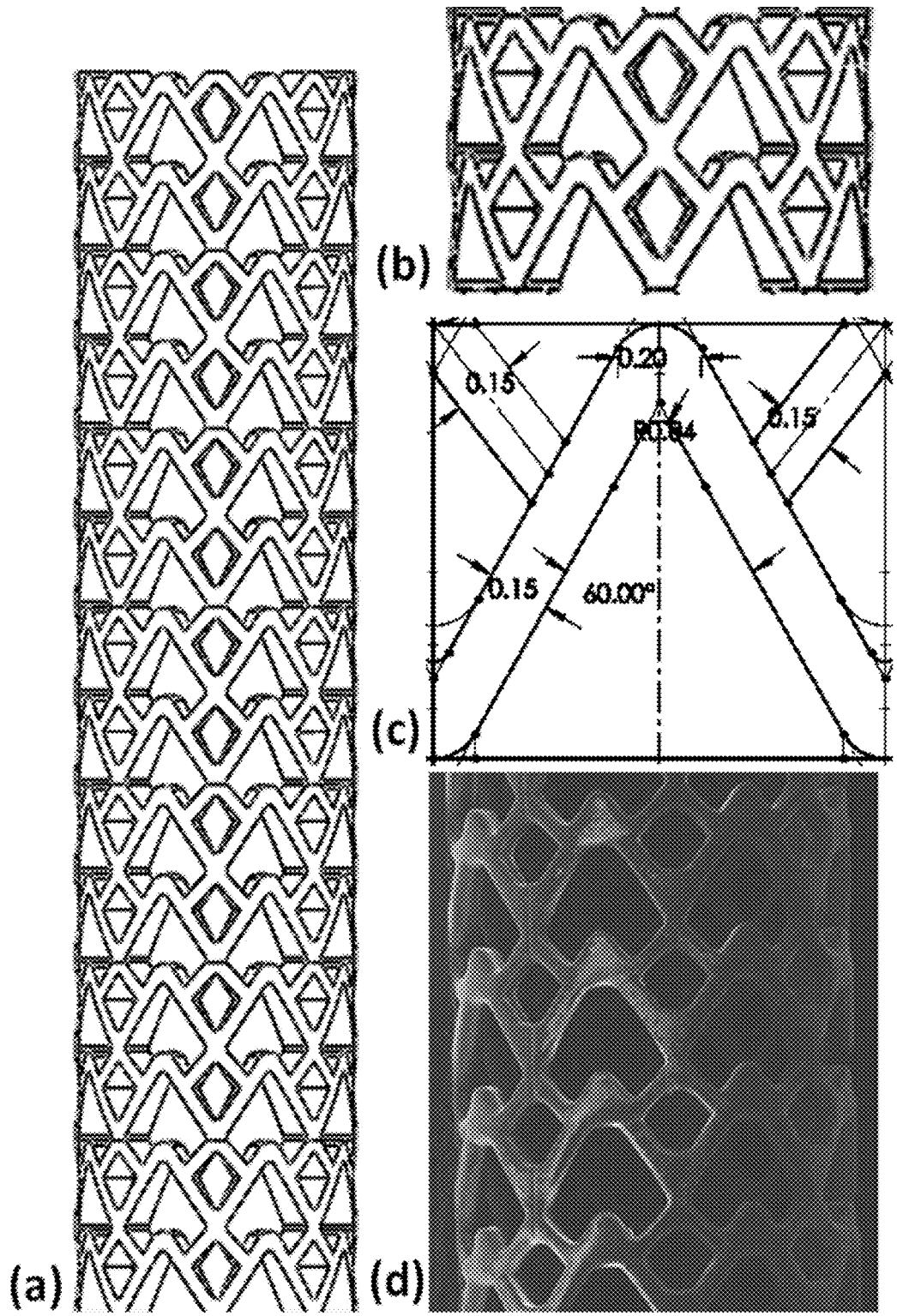
FIG. 12. Arrowhead Design: (a) CAD of full stent (b) CAD of unit length of stent (c) Unit cell design (D) scanning electron micrograph of Arrowhead design after CLIP process.

For greater emphasis on radial strength, another compact design was created with simplified connections between struts. FIG. 12 below shows the CAD drawings as well as SEM micrograph of the Arrowhead stent design. This design also has a 60 degree angle between struts. Connector thickness and smallest tested strut thickness was 150 um. Unit length of the stent consisted of 8 unit cells. Typical unit cell of this design is shown in FIG. 12(*c*). As with the base design, unit lengths of the Arrowhead design could be attached to one another in CAD software until desired length is obtained.

For optimization, metamodels are created of how each design parameter affects the objective and constraint functions. Constraint functions may be failure stresses, patient vessel geometric constraints, and fabrication constraints. Metamodels may be created from data collected via FEM modeling or experimental data. Following is an example of parametric optimization performed on a stent design made during experiments conducted during development of embodiments herein is shown. A parametric flexibility optimization was performed on the Base design template to make a stent for more diverse applications. The previously described stents were mainly designed to favor strength rather than flexibility. Flexibility is a key component of stents, as vasculature may curve suddenly, and the stent needs to be able to be potentially inserted in variety of geometric areas. The design variables that were varied for study were the strut angle (Θ) and the Connector Height (H). The connector thickness (t) was given a fixed relationship with the Connector Height, with t being 20% of the height (FIG. 14(*a*)). Stress analysis was performed using ANSYS FEA software. The objective function that was to be optimized was known as the Flexibility Metric (FM), which was defined as the integral of Moment vs. Curvature index graph (Pant, S.; Bressloff, N W; Limbert, G. *Biomech. Model Mechanobiol.* (2012) 11; incorporated by reference in its entirety). FM represents a value to be minimized as it implies that for a particular curvature index a smaller applied moment is required. Design of experiments was obtained via Latin Hypercubes in iSight optimization software, which gave 20 design points of interest. Nineteen of these points were created in CAD. The design space of (Θ) was chosen to be 40 and 110 degrees and the design space of "H" was chosen to be between 250 um and 1 mm.

Figure 13A:
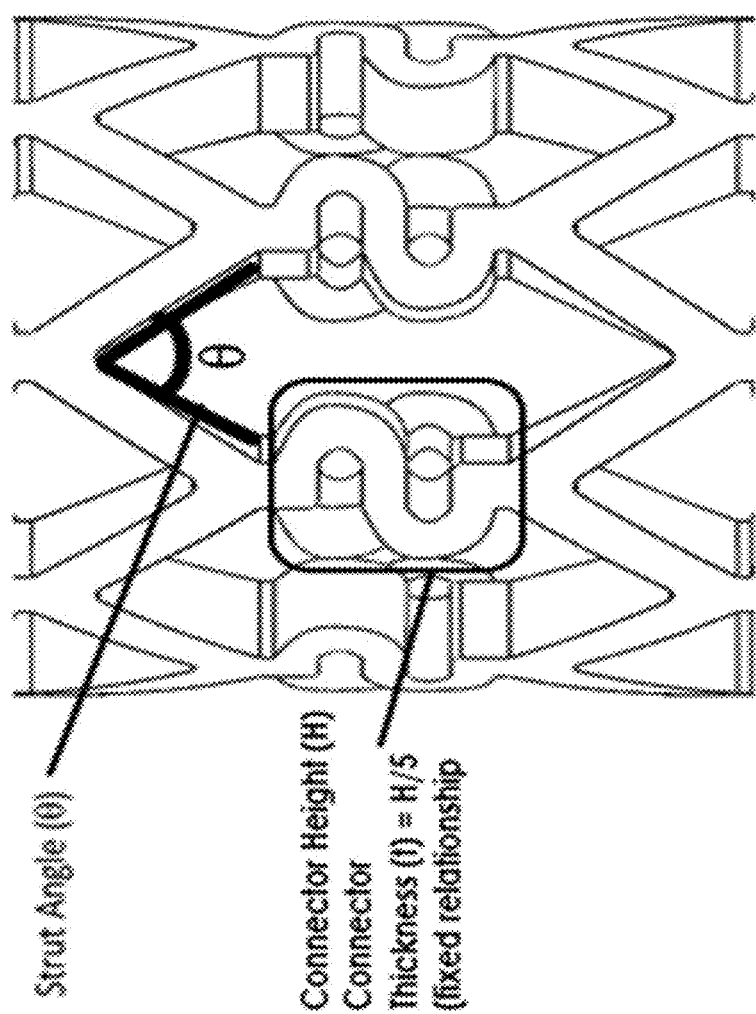
FIGS. 13A-C. Optimization information: (a) Design variables. (b) Flexibility test conditions. (c) Contour graph of Flexibility Metric (FM).
Figure 13B:
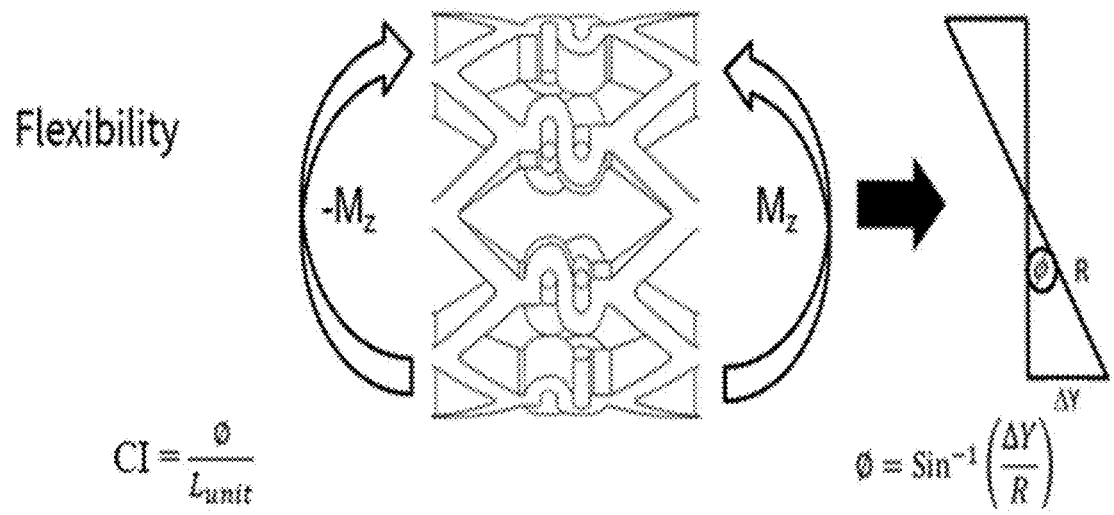
Figure 13C:
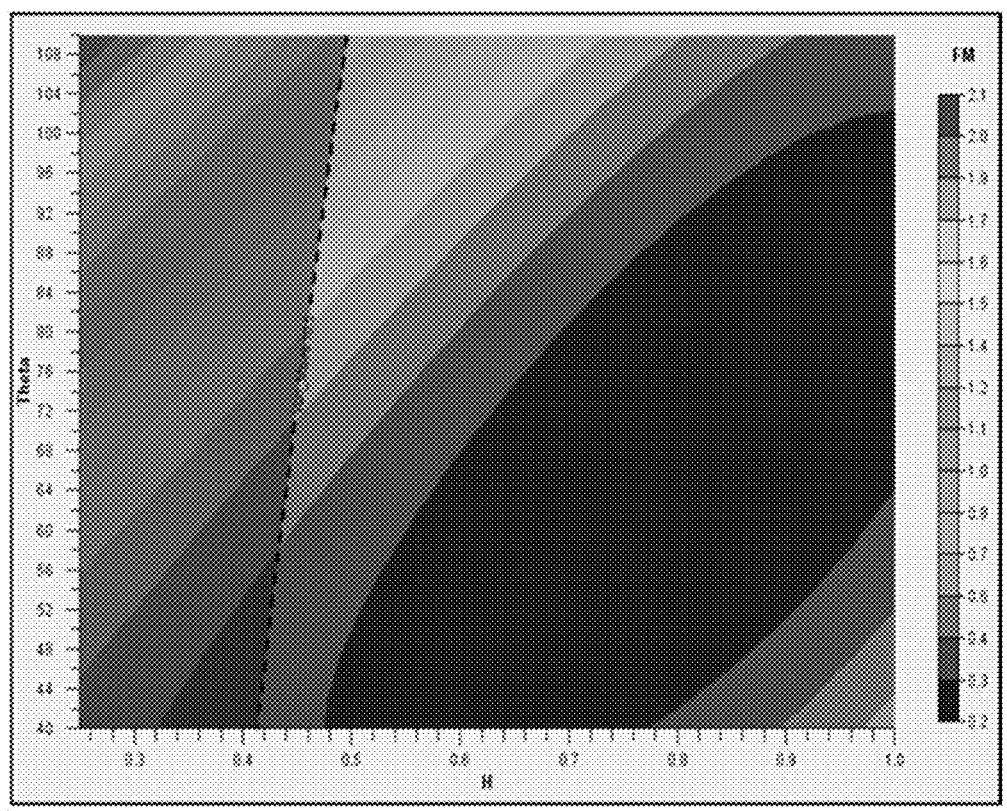
Figure 14:
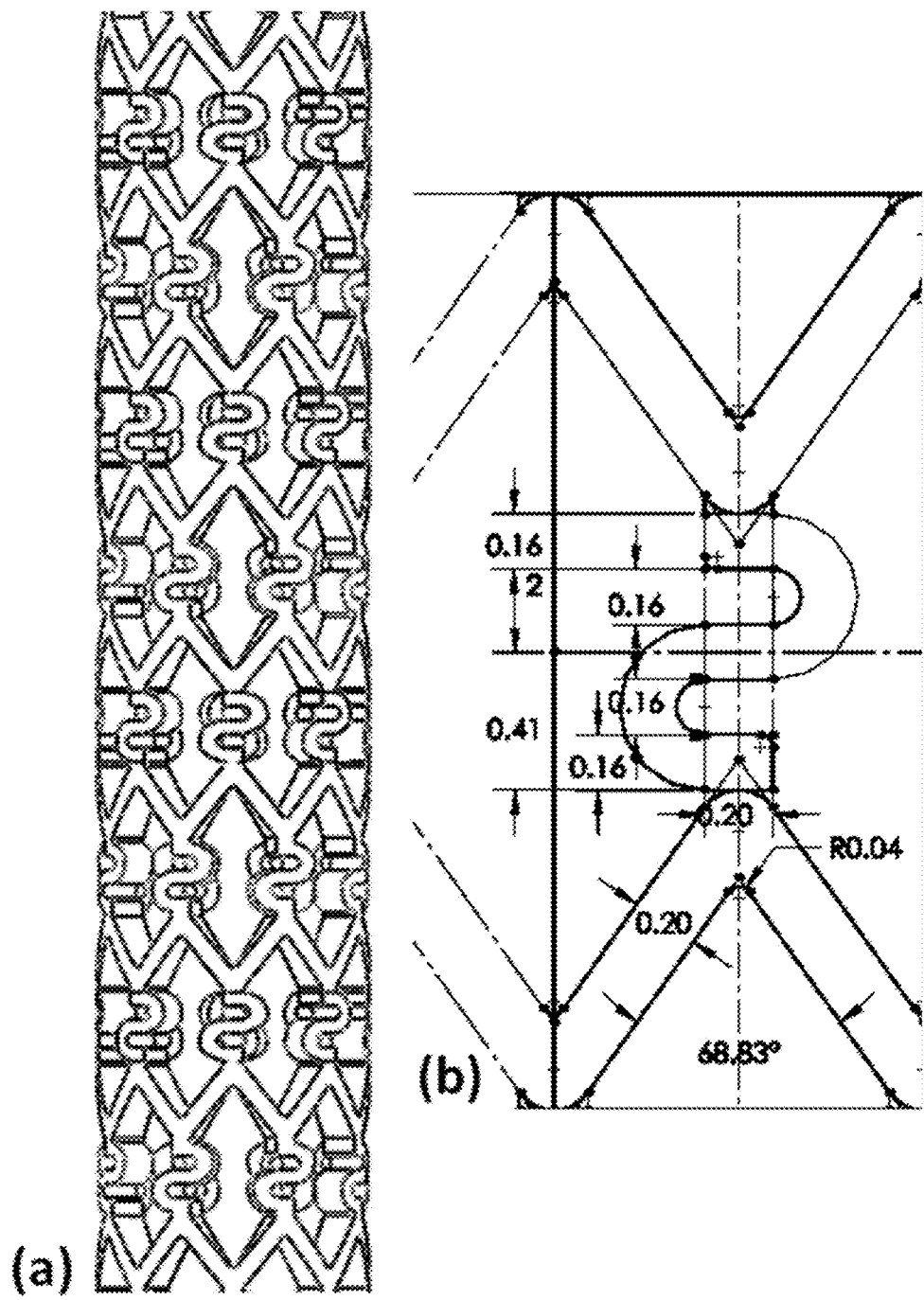
FIG. 14. Flexibility Optimized Base Design: (a) CAD of full length stent (b) Unit cell of stent design.

In ANSYS, a unit length of the stent was subjected to opposing moments (in the out of plane axis) at both axial ends. The moment was varied between 0 to 0.15N*mm. The stent was constrained, such that, one end face was completely fixed, while the opposite end was allowed to deform in the axial direction. The failure criterion was given a failure criterion of 10 MPa. As moments were applied, the von Mises stress and resulting deformation readings were collected. The deformation angle was obtained via the arcsine of the axial deformation divided by the radius of the stent. This value allowed the calculation of the Curvature Index (CI) which was defined as Φ divided by the stent unit length ($L_{unit}$) (FIG. 13(*b*)). A metamodel was created using iSight software and contour plot of the FM was made, which is shown above in FIG. 13(*c*). The gray shaded region to the left of the graph showed where failure by exceeding the 10 MPa was likely. The dark shaded elliptical region represents an area where a minimum of FM could be found. To find this minimum, adaptive simulated annealing and the multi-island genetic algorithms were utilized. Both algorithms appeared to converge to a minimum FM value (FM=4.305E−4), which corresponded to design inputs H=0.825 mm and Θ=68.83 degrees. This optimized design is shown in FIG. 14 below. This design was successfully fabricated. In addition to the values of connector height (H) and strut angle (Θ), this design differed from the "base" design by including thinner wall (400 um), slightly larger strut (200 um) and reduction in circumferential elements (8, rather than 12).

Mechanical Properties

Mechanical tests were performed by mean of radial compression to 25% of the stents' initial outer diameter, using an Instron 5544 mechanical tester according to ISO 25539.

Figure 15:
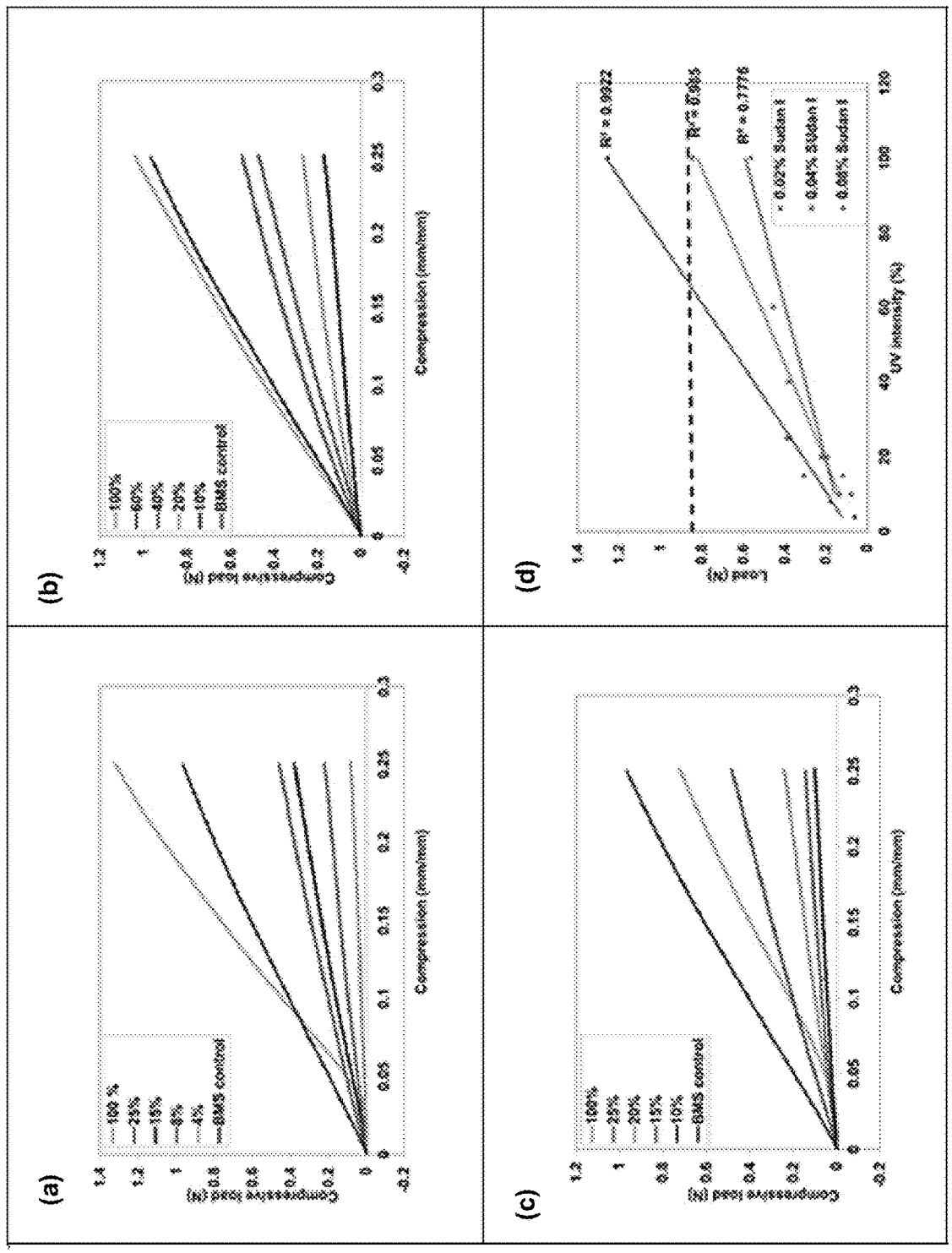
FIG. 15. Radial compression of 3D-printed stents at different UV intensities: A) 50% DEF, 47.78% mPDC, 2.2% Irgacure 819 and 0.02% Sudan I, B) 50% DEF, 47.76% mPDC, 2.2% Irgacure 819 and 0.04% Sudan I, C) 50% DEF, 47.72% mPDC, 2.2% Irgacure 819 and 0.08% Sudan I, and D) Radial compressive load at 20% radial compression for all stents. Black dashed line indicates the target radial load of a control bare-metal nitinol stent. Stents were post-cured at 2×2.5 minutes.

In FIG. 15, it can be seen that the radial strength of stent can be increased by increasing the UV intensity used during printing. The radial strength decreases with an increase in Sudan I concentration, giving flexibility in strength by changing the UV absorber content.

Figure 16:
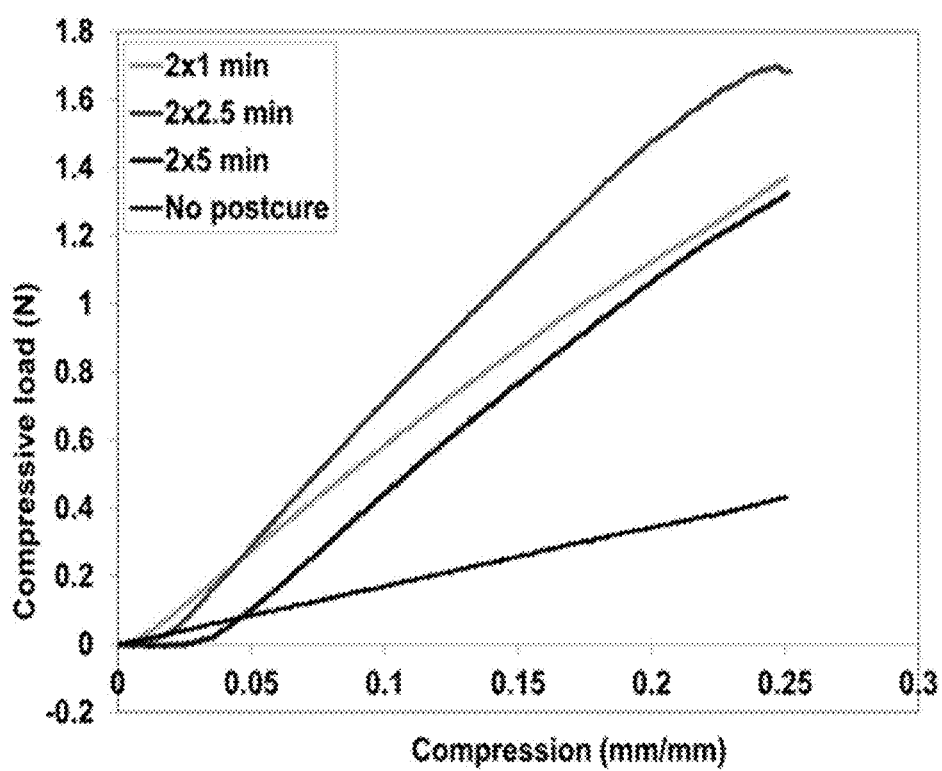
FIG. 16. Effect of post-curing time on mechanical strength of stents. All stents were printed with biomaterial ink of following composition: 50% DEF, 47.78% mPDC, 2.2% Irgacure 819 and 0.02% Sudan I. UV intensity for printing process was 100%.

From the FIG. 16, it can be seen that post-curing more than doubles the mechanical strength of the 3D-printed biomaterial ink stents, but that the post-curing time barely affects the mechanical properties. Thus, the majority of flexibility in mechanical properties is possible at the printing stage.

Figure 17:
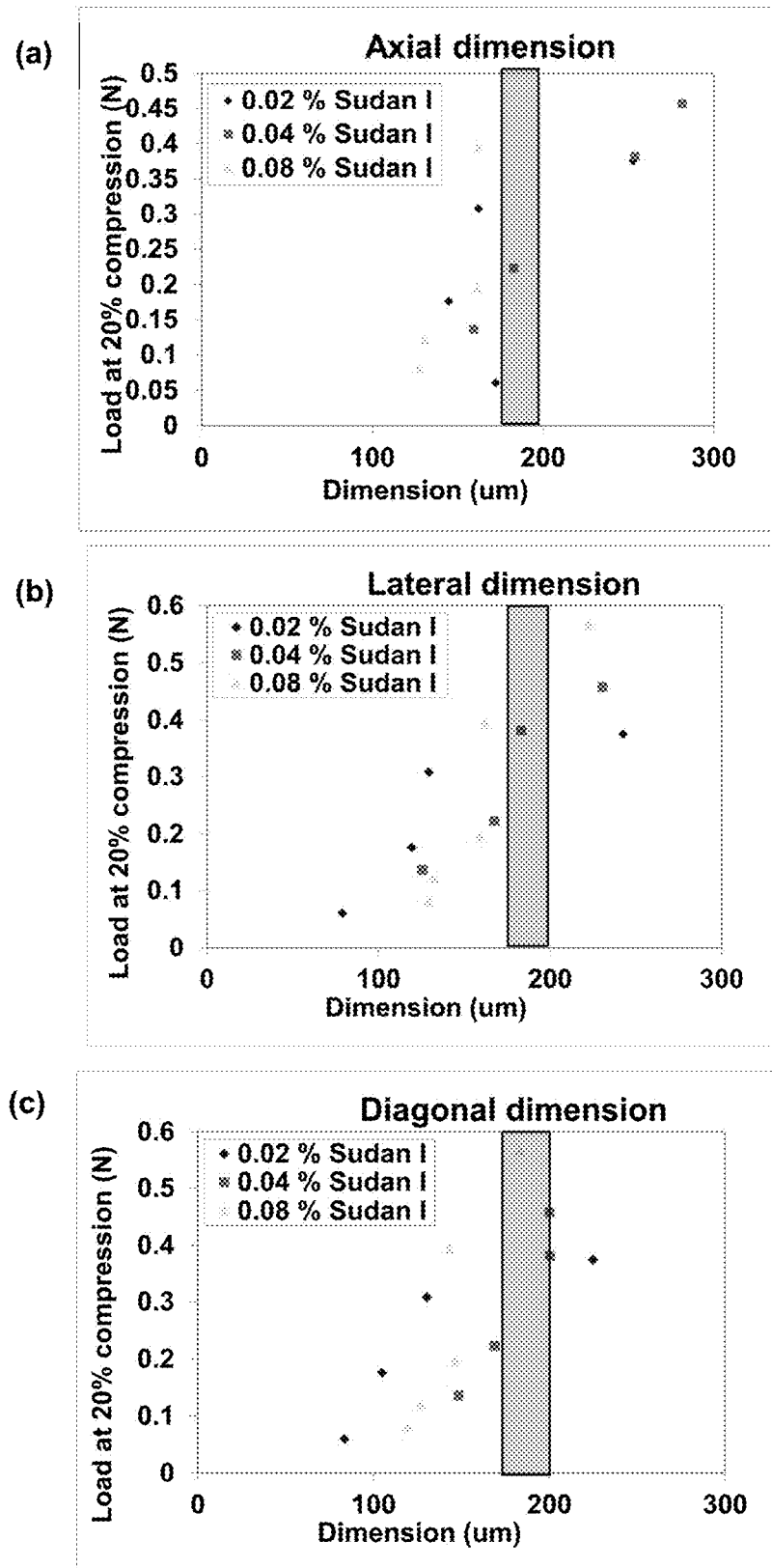
FIG. 17. Relation between stent dimensions and radial compressive load at 20% radial compression: A) Axial dimension, B) Lateral dimension and C) Diagonal dimension. All stents were printed from biomaterial ink of following composition: 50% DEF, 2.2% Irgacure 819, and mPDC and Sudan I adding up to 47.8% together. Shaded box indicates the target dimensions, comparable to currently developed bioresorbable stents. Stents were 3D-printed at various UV intensities, but all were post-cured at 2×2.5 minutes.

As can be seen in FIG. 17, there is a strong correlation between the dimensional and mechanical properties of stents, indicating that a larger material footprint increases radial strength of stents. However, the relative content of UV absorber affects the nature of the correlation. Generally, higher UV absorber concentrations lead to a faster increase in mechanical strength with increasing dimensions.

Figure 18:
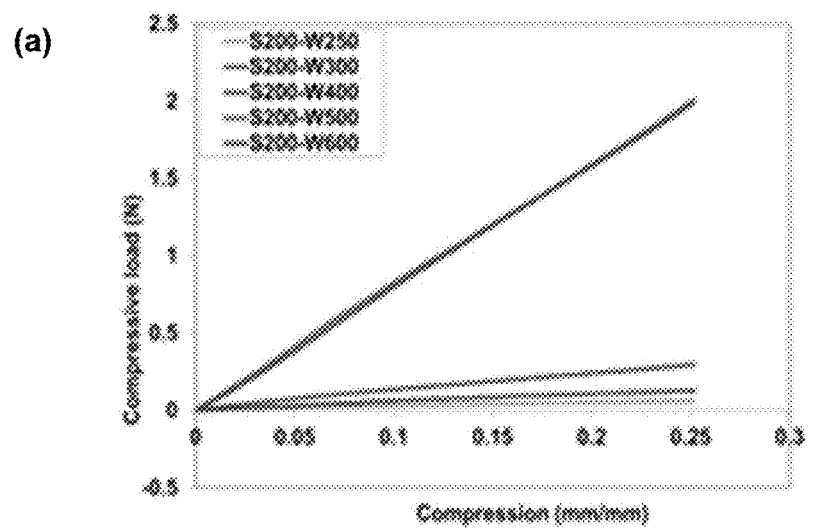
FIG. 18. Mechanical properties of Arrowhead design stents: A) Dependency on the wall thickness varying between 250-600 um, B) Dependency on the strut dimensions varying between 150-200 um. Stents were printed from biomaterial ink of following composition: 50% DEF, 2.2% Irgacure 819, 47.72% mPDC and 0.08% Sudan I. Stents were postcured at 2×2.5 minutes.
Figure 18:
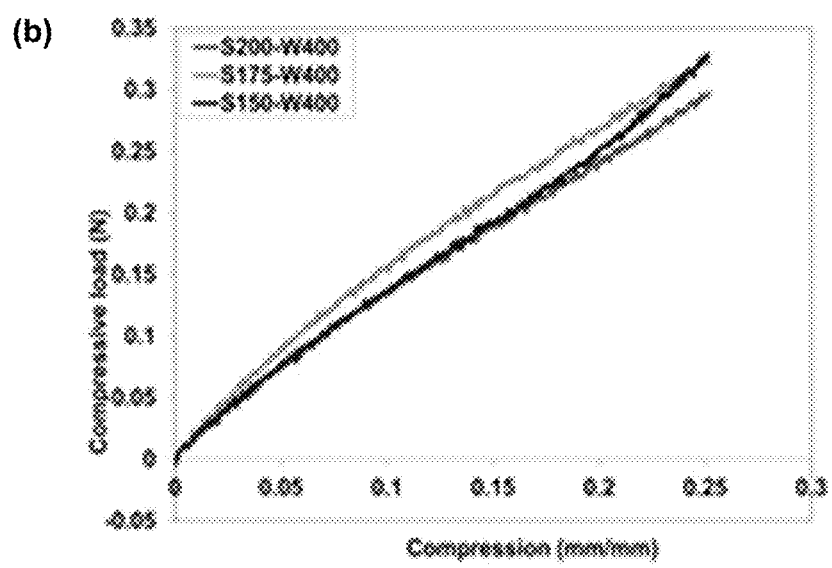

FIG. 18 demonstrates that for the Arrowhead design the radial strength does not depend on the strut dimensions, but is strongly dependent on the wall thickness.

Figure 19:
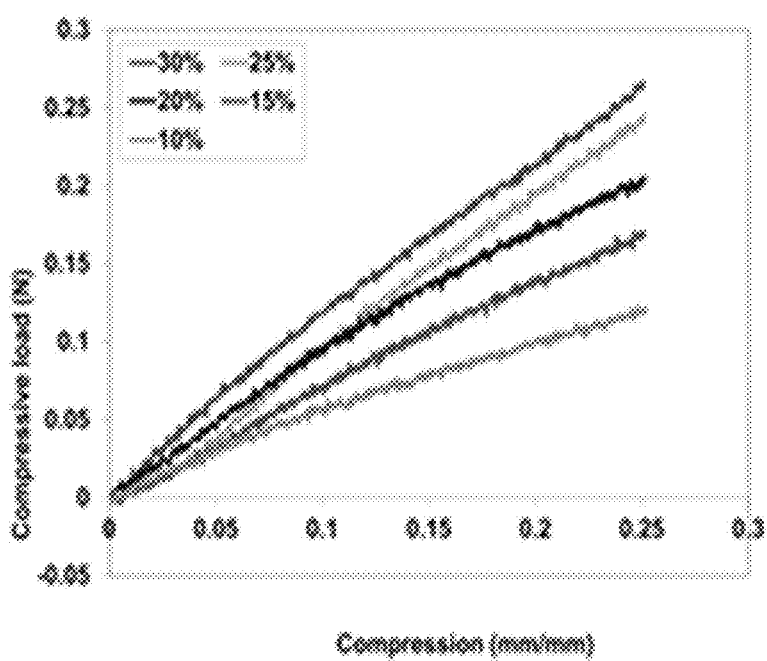
FIG. 19. Mechanical properties of biomaterial ink with added accelerator compound. Stents were printed from biomaterial ink of following composition: 50% DEF, 1% Irgacure 819, 47.92% mPDC, 0.08% SUdan I and 1% Ethyl-4-Dimethylamine Benzoate (EDAB). Stents were 3D-printed at various UV intensities, but were post-cured at 2×2.5 minutes.

FIG. 19 indicates that biomaterial ink stents may be printed using an accelerator compound like EDAB. EDAB accelerates the rate of radical formation for polymerization initiation.

REFERENCES

The following references, some of which are cited above by number, are herein incorporated by reference in their entireties.

1. Gundogan, B., et al., *Bioabsorbable Stent Quo Vadis: A Case for Nano-Theranostics*. Theranostics, 2014. 4(5): p. 514-533.
2. Ulrich Sigwart, M.D., Jacques Puel, M.D., Velimir Mirkovitch, M.D., Francis Joffre, M.D., and Lukas Kappenberger, M.D., *Intravascular Stents to Prevent Occlusion and Re-Stenosis after Transluminal Angioplasty*. New England Journal of Medicine, 1987. 316: p. 6.
3. Serruys P W, K. M., Ong A T., *Coronary-artery stents*. New England Journal of Medicine, 2000. 354: p. 13.
4. Hermawan, H., D. Dube, and D. Mantovani, *Developments in metallic biodegradable stents*. Acta Biomater, 2010. 6(5): p. 1693-7.
5. Regar E, S. G., Serruys P W., *Stent development and local drug delivery*. British Medical Bulletin, 2001. 59: p. 21.
6. Ranade S V, M. K., Richard R E, Chan A K, Allen M J, Hel-mus M N., *Physical characterization of controlled release of paclitaxel from the TAXUS Express drug-eluting stent*. J Biomed Mater Res, 2004. 71A: p. 10.
7. Schmitz K P, G. N., Lobler M, Behrend D, Schmidt W, Sternberg K., *Drug-eluting stent technologies for vascular regeneration*. International Journal of Materials research, 2007. 98: p. 6.
8. Kedia G, L. M., *Stent thrombosis with drug-eluting stents: a re-examination of the evidence*. Catheter cardiovascular intervention, 2007. 69: p. 8.
9. Garg S, S. P., *Coronary stents: looking forward*. Journal of the American College of Cardiology, 2010. 56: p. 34.
10. Mei-Chin Chen, H. W. T., Yen Chang, Wei-Yun Lai, Fwu-Long Mi, Chin-Tang Liu, Hen-Sheng Wong, and Hsing-Wen Sung, *Rapidly self expandable polymeric stents with shape memory property*. Biomacromolecules, 2007. 8: p. 7.
11. Grabow, N., et al., *A biodegradable slotted tube stent based on poly(L-lactide) and poly(4-hydroxybutyrate) for rapid balloon-expansion*. Ann Biomed Eng, 2007. 35(12): p. 2031-8.
12. Shih-Jung Liu, F. J. C., Chao-Ying Hsiao, Yi-Chuan Kau, Kuo-Sheng Liu, *Fabrication of Balloon-Expandable Self-Lock Drug-Eluting Polycaprolactone Stents Using Micro-Injection Molding and Spray Coating Techniques*. Annal of Biomedical Engineering, 2010. 38(10): p. 9.
13. Ormiston, J. A. and P. W. Serruys, *Bioabsorbable coronary stents*. Circ Cardiovasc Interv, 2009. 2(3): p. 255-60.
14. Garg, S., C. Bourantas, and P. W. Serruys, *New concepts in the design of drug-eluting coronary stents*. Nat Rev Cardiol, 2013. 10(5): p. 12.
15. Yang, J., et al., *Haemo-and cytocompatibility of bioresorbable homo-and copolymers prepared from 1,3-trimethylene carbonate, lactides, and epsilon-caprolactone*. J Biomed Mater Res A, 2010. 94(2): p. 396-407.
16. Yang, J., et al., *Hydrolytic and enzymatic degradation of poly(trimethylene carbonate-co-d,l-lactide) random copolymers with shape memory behavior*. European Polymer Journal, 2010. 46(4): p. 783-791.
17. Subbu S Venkatraman, Lay Poh Tan, Joe Ferry D Joso, Yin Chiang Freddy Boey, Xintong Wang., *Biodegradable stents with elastic memory*. Biomaterials, 2006. 27(32): p. 5.
18. Umeda, K. I. a. N., *Rapid prototyping in Biomedical Engineering, Advanced Applications of Rapid Prototyping Technology in Modern Engineering*. 2011.
19. Rengier, F., A. Mehndiratta, H. Tengg-Kobligk, C. M. Zechmann, R Unterhinninghofen, H. and a. F. L. G. U. Kauczor, *3D printing Based on Imaging Data: Review of Medical Applications*. International Journal of Computer Assisted Radiology and Surgery., 2010. 5(4): p. 6.
20. Melgoza, E. L., Guillem Vallicrosa, Lidia Sereno, Joaquim Ciurana, and Ciro A. and Rodriguez., *Rapid Tooling Using 3D Printing System for Manufacturing of Customized Tracheal Stent*. Rapid Prototyping Journal, 2013. 20(1): p. 10.
21. Lim, C. S., P. Eng, S. C. Lin, C. K. Chua, and Y. T. Lee., *Rapid Prototyping and Tooling of Custom-made Tracheobronchial Stents*. The International Journal of Advanced Manufacturing Technology, 2002. 20(1): p. 5.
22. Park, S. A., Sang J. Lee, Kyung S. Lim, In H. Bae, Jun H. Lee, Wan D. Kim, Myung H. and a. J. K. P. Jeong, *In vivo evaluation and characterization of a bioabsorbable drug-coated stent fabricated using a 3D printing system*. Materials Letters, 2015. 141: p. 4.
23. Kun Sun, K. S., Qimao Feng, *Slide fastener bioabsorbable stent and application thereof*. US20130226277 A1, 2013.
24. Sun, C., et al., *Projection micro-stereolithography using digital micro-mirror dynamic mask*. Sensors and Actuators A: Physical, 2005. 121(1): p. 113-120.
25. Baker, E., et al., *Microstereolithography of Three-Dimensional Polymeric Springs for Vibration Energy Harvesting*. Smart Materials Research, 2012. 2012: p. 1-9.
26. Yang, J., et al., *Synthesis and evaluation of poly(diol citrate) biodegradable elastomers*. Biomaterials, 2006. 27(9): p. 1889-98.
27. Serrano, M. C., L. Carbajal, and G. A. Ameer, *Novel biodegradable shape-memory elastomers with drug-releasing capabilities*. Adv Mater, 2011. 23(19): p. 2211-5.
28. Yang, J., et al., *A thermoresponsive biodegradable polymer with intrinsic antioxidant properties*. Biomacromolecules, 2014. 15(11): p. 3942-52.

The invention claimed is:

1. A method of 3D printing an object by continuous liquid interface production (CLIP) with a biomaterial ink, comprising:
(a) providing a pool of a photo-curable biomaterial ink, wherein the photo-curable biomaterial ink comprises: methacrylated poly(diol citrate) and the poly(diol citrate) comprises a polymer of citric acid and HO—$(CH_2)_n$—OH, wherein n is 2-20, and wherein the bottom of the pool is transparent to ultraviolet (UV) light;
(b) exposing the transparent bottom of the pool to UV light in the 2D shape of a cross-section of the object; wherein the UV light converts a layer of the photo-curable biomaterial ink into solidified biomaterial layer in the shape of the cross-section of the object;

(c) raising the solidified biomaterial layer in the pool and allowing the photo-curable biomaterial ink to flow under the solidified biomaterial layer;

(d) repeating steps (b) and (c) with successive cross-sectional layers to produce the object.

2. The method of claim 1, wherein the photo-curable biomaterial ink further comprises one or more of: a solvent, a photoinitiator, a co-initiator, a free-radical quencher, and a UV-absorber.

* * * * *